United States Patent
Mortensen et al.

(10) Patent No.: US 6,936,222 B2
(45) Date of Patent: Aug. 30, 2005

(54) METHODS, APPARATUSES, AND APPLICATIONS FOR COMPLIANT MEMBRANE BLOOD GAS EXCHANGERS

(75) Inventors: J. D Mortensen, Sandy, UT (US); Robert N. Schaap, Salt Lake City, UT (US); Barry Bagley, Salt Lake City, UT (US)

(73) Assignee: Kenneth L. Franco, Peoria, IL (US)

( * ) Notice: Subject to any disclaimer, the term of this patent is extended or adjusted under 35 U.S.C. 154(b) by 273 days.

(21) Appl. No.: 10/244,181

(22) Filed: Sep. 13, 2002

(65) Prior Publication Data

US 2004/0052681 A1 Mar. 18, 2004

(51) Int. Cl.⁷ ............................ A61M 1/36; A61M 37/00
(52) U.S. Cl. ........................ 422/45; 422/44; 604/6.14; 128/DIG. 3; 261/DIG. 28
(58) Field of Search .................. 422/44–48; 604/4.01, 604/6.11, 6.14, 6.15, 6.13; 128/DIG. 3; 96/4–11, 243, 255, 267, 296, 299; 95/43, 45, 54, 149, 291; 435/283.1, 284.1, 289.1, 297.4; 523/1, 103, 105, 112, 200, 222, 310; 261/DIG. 28; 210/321.6, 321.79, 321.8, 321.88

(56) References Cited

U.S. PATENT DOCUMENTS

| | | | |
|---|---|---|---|
| 3,626,950 A | 12/1971 | Schulte | |
| 4,576,590 A | 3/1986 | Fiddian-Green | |
| 4,583,969 A | 4/1986 | Mortensen | |
| 4,610,656 A | 9/1986 | Mortensen | |
| 4,625,712 A | 12/1986 | Wampler | |
| 4,632,107 A | 12/1986 | Butler | |
| 4,704,121 A | 11/1987 | Moise | |
| 4,753,221 A | 6/1988 | Kensey et al. | |
| 4,779,614 A | 10/1988 | Moise | |
| 4,817,586 A | 4/1989 | Wampler | |
| 4,846,152 A | 7/1989 | Wampler et al. | |
| 4,850,958 A | 7/1989 | Berry et al. | |
| 4,895,557 A | 1/1990 | Moise et al. | |
| 4,906,229 A | 3/1990 | Wampler | |
| 4,908,012 A | 3/1990 | Moise et al. | |
| 4,944,722 A | 7/1990 | Carriker et al. | |

(Continued)

FOREIGN PATENT DOCUMENTS

| | | |
|---|---|---|
| EP | 0 631 790 | 1/1995 |
| EP | 0480101 | 5/1996 |
| EP | 0569319 | 9/1997 |
| EP | 0697221 | 12/1998 |
| WO | WO 89/05164 | 6/1989 |
| WO | WO 92/17118 | 10/1992 |
| WO | WO 00/62837 | 10/2000 |

*Primary Examiner*—Patricia Bianco
(74) *Attorney, Agent, or Firm*—Gifford, Krass, Groh, Sprinkle, Anderson & Citkowski, P.C.

(57) ABSTRACT

A compliant blood gas exchanger is provided including a housing having a first end cap, a second end cap, and an elastomeric sidewall or sleeve extending there between forming a chamber. A hollow fiber assembly is disposed in the chamber. The hollow fiber assembly has a first mounting collar, a second mounting collar and a plurality of hollow fibers disposed there between. The first end cap is disposed in communication with the first mounting collar and the second end cap is disposed in communication with the second mounting collar. The end caps are connected to a gas inlet and a gas outlet. The chamber is in communication with a blood inlet and a blood outlet. The elastomeric sidewall is responsive to internal and external pressures affecting the chamber. The first chamber can also be placed adjacent to a second chamber and both chambers placed within a rigid outer housing. Thus, a dual-chamber pulsatile blood gas exchanger can be provided. That is, the second chamber may be in connection with a pump mechanism or vacuum mechanism such that the chamber creates a pulsatile flow within the first chamber.

13 Claims, 9 Drawing Sheets

U.S. PATENT DOCUMENTS

| | | | |
|---|---|---|---|
| 4,986,809 A | 1/1991 | Hattler | |
| 5,037,383 A | 8/1991 | Vaslef et al. | |
| 5,061,256 A | 10/1991 | Wampler | |
| 5,092,844 A | 3/1992 | Schwartz et al. | |
| 5,098,376 A | 3/1992 | Berry et al. | |
| 5,125,902 A | 6/1992 | Berry et al. | |
| 5,158,534 A | 10/1992 | Berry et al. | |
| 5,158,553 A | 10/1992 | Berry et al. | |
| 5,182,317 A * | 1/1993 | Winters et al. | 523/112 |
| 5,219,326 A | 6/1993 | Hattler | |
| 5,230,862 A | 7/1993 | Berry et al. | |
| 5,262,451 A | 11/1993 | Winters et al. | |
| 5,308,314 A | 5/1994 | Fukui et al. | |
| 5,336,164 A | 8/1994 | Snider et al. | |
| 5,338,770 A | 8/1994 | Winters et al. | |
| 5,342,693 A | 8/1994 | Winters et al. | |
| 5,393,207 A | 2/1995 | Maher et al. | |
| 5,487,727 A | 1/1996 | Snider et al. | |
| 5,501,663 A | 3/1996 | Hattler et al. | |
| 5,814,011 A | 9/1998 | Corace | |
| 5,827,304 A | 10/1998 | Hart | |
| 5,865,789 A | 2/1999 | Hattler | |
| 6,682,698 B2 * | 1/2004 | Chambers et al. | 422/45 |
| 2002/0143397 A1 * | 10/2002 | von Segesser | 623/9 |

* cited by examiner

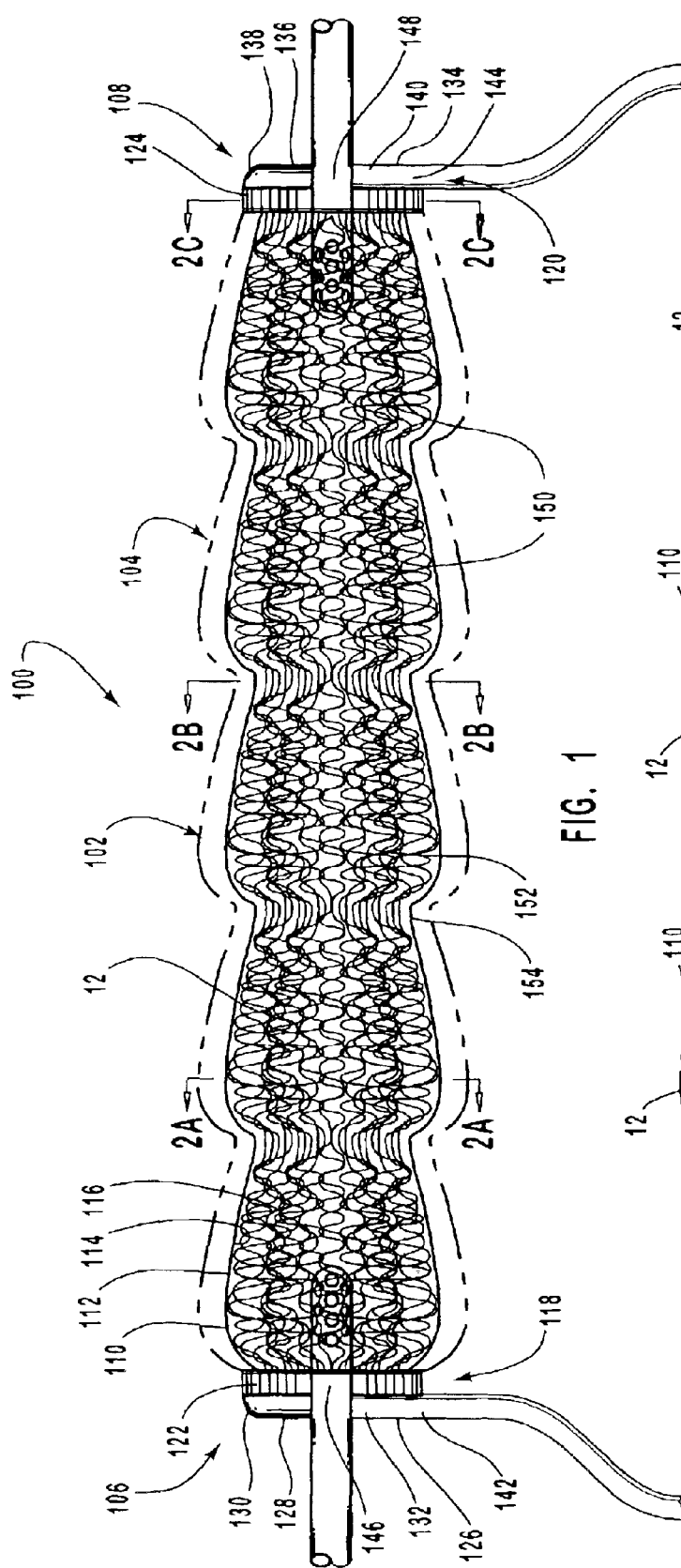
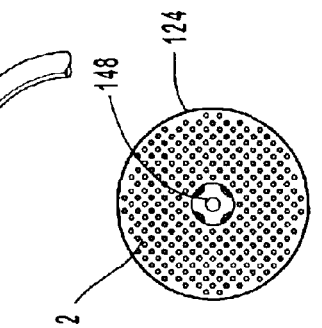
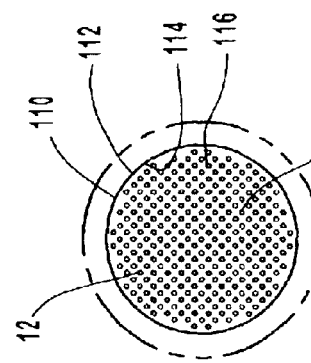
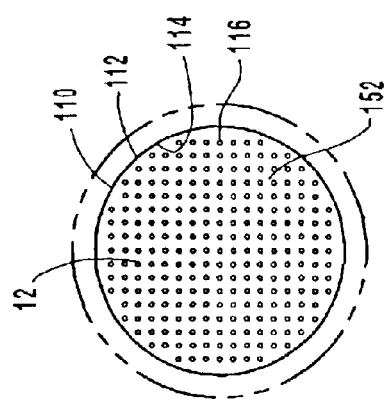
FIG. 1
FIG. 2A
FIG. 2B
FIG. 2C

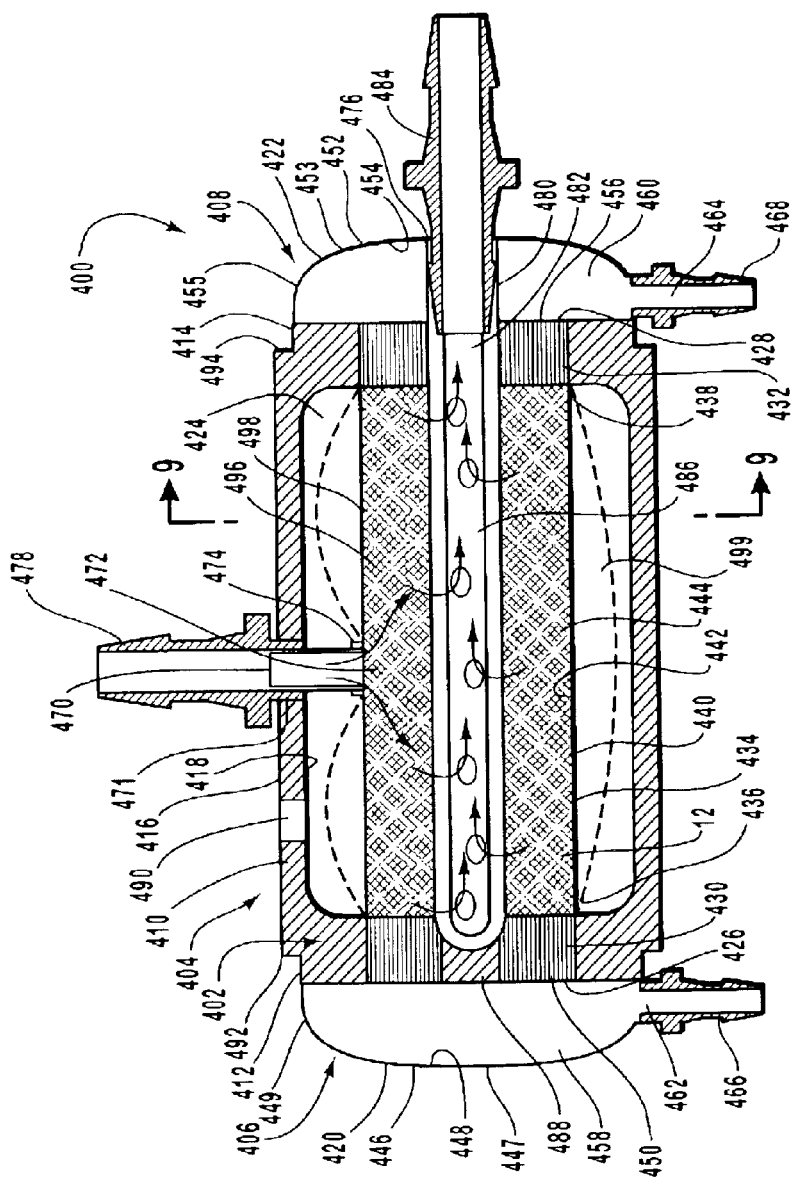
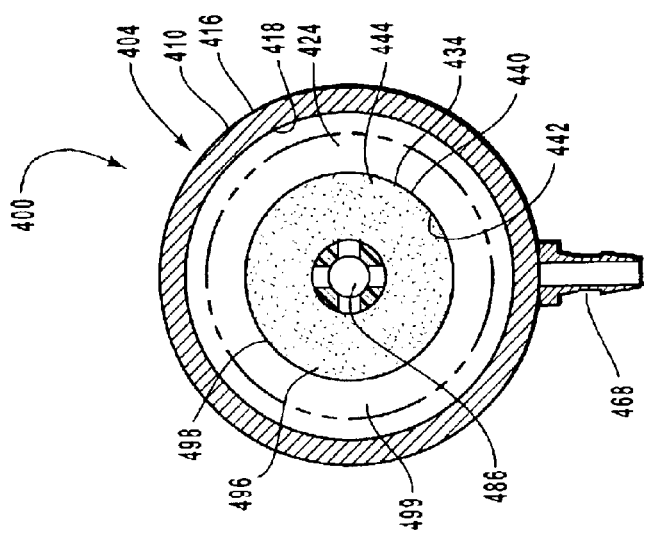
FIG. 8
FIG. 9

METHODS, APPARATUSES, AND APPLICATIONS FOR COMPLIANT MEMBRANE BLOOD GAS EXCHANGERS

BACKGROUND OF THE INVENTION

1. The Field of the Invention

The present invention relates generally towards a lung assist device that transports oxygen into and carbon dioxide out of the circulating venous blood. More particularly, the present invention is directed towards a compliant blood gas exchanger which can be used intracorporeally or extracorporeally to efficiently, effectively, and safely exchange oxygen and carbon dioxide for patients with advanced respiratory failure.

2. The Relevant Technology

Thousands of people suffer from inadequate blood gas exchange, which includes both inadequate input of oxygen and inadequate removal of carbon dioxide from the blood. Inadequate blood gas exchange can be caused by many conditions or illnesses such as pneumonia, pneumonitis, atelectasis, various heart and circulatory ailments, blood in the lungs, obstruction of pulmonary ventilation, acute respiratory distress syndrome, or lung injury caused by heat, noxious gases and other factors.

One alternative to treating advanced respiratory ailments is to opt for a lung transplant. This is expensive and risky for the patient. Hence, lung assist devices are a preferred method of treating respiratory disease. There are several types of conventional lung assist devices that supply oxygen to and remove carbon dioxide from patient's blood for short term. These devices can be conveniently separated into three categories: respirators, extracorporeal oxygenators and intravascular lung assist devices. In general, respirators are useful in improving the efficiency of a patient's blood gas exchange when used judiciously in low or moderate intensity. However, respirators are not suitable for use where a patient's damaged or diseased lungs require rest or are simply incapable of performing the required respiration. They are also not suitable for high-intensity blood gas exchanges (high pressure, gas flow rate, and/or concentration of oxygen).

Extracorporeal oxygenators, commonly referred to as heart-lung machines, usually take the form of extracorporeal membrane oxygenators (ECMOs) and are most frequently used for relatively short intervals, such as during surgery where the circulation through a patient's heart and lungs is temporarily bypassed. Extracorporeal oxygenators are generally not used for extended or long-term critical care because the machines are expensive to operate and require almost constant supervision and monitoring by skilled technicians. Conventional heart-lung machines also require systemic administration of anticoagulants, which may create additional problems such as internal bleeding, especially when systematically administered on a long-term basis.

Extracorporeal membrane oxygenators typically include a gas permeable membrane in which oxygen-rich gas flows on one side of the membrane and blood flows on the other side. As the blood flows along one side of the membrane, oxygen supplied to the other side of the membrane permeates through the membrane into the blood while carbon dioxide permeates through the membrane from the blood into the gas on the other side of the membrane. Oxygen will diffuse or travel across the membrane and enter the blood if there is a sufficient pressure gradient between the oxygen supply and the blood. In addition, carbon dioxide will diffuse from the blood, across the membrane, and into the gas chamber. The membrane separating the blood from the gas allows blood gas exchange of the blood without introducing oxygen bubbles into the blood. The gas permeable membrane is typically either a microporous membrane that allows gas to exchange through the micropores or a continuous membrane that allows gas to exchange through the membrane without the gas and blood directly interfacing.

Respirators and ECMOs, however, place more strain on the lungs, which may be diseased or injured and unable to function at full capacity. In order to allow diseased or damaged lungs to heal, it is desirable to allow the lungs to rest and then gradually increase their function. Because conventional respirators place more strain and require more work from the lungs, this often prevents the lungs from healing or recovering. Additionally, these machines are often used in late stages of respiratory failure when patients have multi-organ failure from the inadequate blood gas exchange and any additional stress to a patient could be critical.

Intravascular lung assist devices have also been developed to provide blood gas exchange in patients with respiratory failure. However, intravascular lung assist devices can provide only a portion of the blood gas exchange requirements of a patient with advanced lung failure. Furthermore, they have not been used continuously for more than 6 to 8 weeks.

Thus, it would be an improvement in the art to have an blood gas exchangers which (1) are small enough to be portable and/or implantable; (2) is employable either extracorporeally and intracorporeally; (3) compliant enough to present high systolic blood pressure peaks when receiving blood pumped by the patient's right or left ventricle; (4) provides a physiologically compatible blood flow rate and pattern; (5) is safe and easy to use; (6) is sufficiently non-thrombogenic and biocompatible with the blood such that systemic anticoagulation during use of the blood gas exchanger is not necessary; (7) is amenable to automatic control by servo mechanisms; and (8) provides more efficient and longer term gas exchange than is currently available in the art.

BRIEF SUMMARY OF THE INVENTION

The present invention addresses the above-described needs in the art as well as providing other benefits. A compliant blood gas exchanger is provided having a housing comprising a first end, a second end, and a sidewall extending there between. The first end of the housing terminates in a first end cap and the second end of the housing terminates in a second end cap. Disposed within the housing of the compliant blood gas exchanger is a hollow fiber assembly. In one embodiment, the hollow fiber assembly has a first mounting collar and a second mounting collar and a plurality of hollow fibers disposed there between. The first end cap is connected to the first mounting collar and a second end cap is connected to the second mounting collar. The end caps are connected to a gas inlet and a gas outlet. The chamber is in communication with a blood inlet and a blood outlet. Thus, a gas flow circuit and a blood flow circuit are formed between which blood gas exchange occurs via the hollow fibers. In addition, the elastomeric sidewall is responsive to internal and external pressures applied to the chamber.

The compliant blood gas exchanger may be used intracorporeally as an implantable respiratory prosthesis. In such an embodiment, the compliant blood gas exchanger may serve as an implantable intrathoracic artificial lung. In another embodiment, the compliant blood gas exchanger may be used as a pumpless arterio-venous shunt.

The chamber of the compliant blood gas exchanger (the first chamber) can also be placed adjacent to a second chamber and both chambers placed within a rigid outer housing. Thus, a dual-chamber pulsatile blood gas exchanger can be provided. That is, the second chamber may be in connection with a pump mechanism or vacuum mechanism such that an increase or decrease of pressure in the second chamber creates a pulsatile flow within the first chamber. The pulsatile flow is more biocompatible with the cardiopulmonary system of the patient than a continuous blood flow. In one embodiment, the compliant blood gas exchanger can be combined with a cannulae system for synchronizing the blood pulse of the patient with the pulsatile flow of the exchanger.

Alternatively, the dual-chamber blood gas exchanger can be made portable for use as an extracorporeal perfusion system for prolonged ECMO, ECLA, ELS, or ECCO2R, emergency life support perfusion systems, or for long-term support of patients in cardiorespiratory failure.

These and other objects and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only typical embodiments of the invention and are therefore not to be considered limiting of its scope. The invention will be described and explained with additional specificity and detail through the use of the accompanying drawings in which:

FIG. 1 is a front elevational view of a compliant blood gas exchanger in accordance with an embodiment of the present invention, illustrating a bundle of crimped and segmented fibers disposed within a compliant housing;

FIG. 2A is a cross-sectional view of the compliant blood gas exchanger shown in FIG. 1 taken along line 2A—2A;

FIG. 2B is a cross-sectional view of the compliant blood gas exchanger shown in FIG. 1 taken along line 2B—2B;

FIG. 2C is a cross-sectional view of the compliant blood gas exchanger shown in FIG. 1 taken along line 2C—2C;

FIG. 8 is a side elevational view of a compliant blood gas exchange system in accordance with another embodiment of the present invention, illustrating a compliant blood gas exchanger disposed in a rigid housing;

FIG. 9 is a cross-sectional view of the heart/lung blood gas exchanger shown in FIG. 8 taken along line 9—9;

DETAILED DESCRIPTION OF THE PREFERRED EMBODIMENTS

Figure 3:
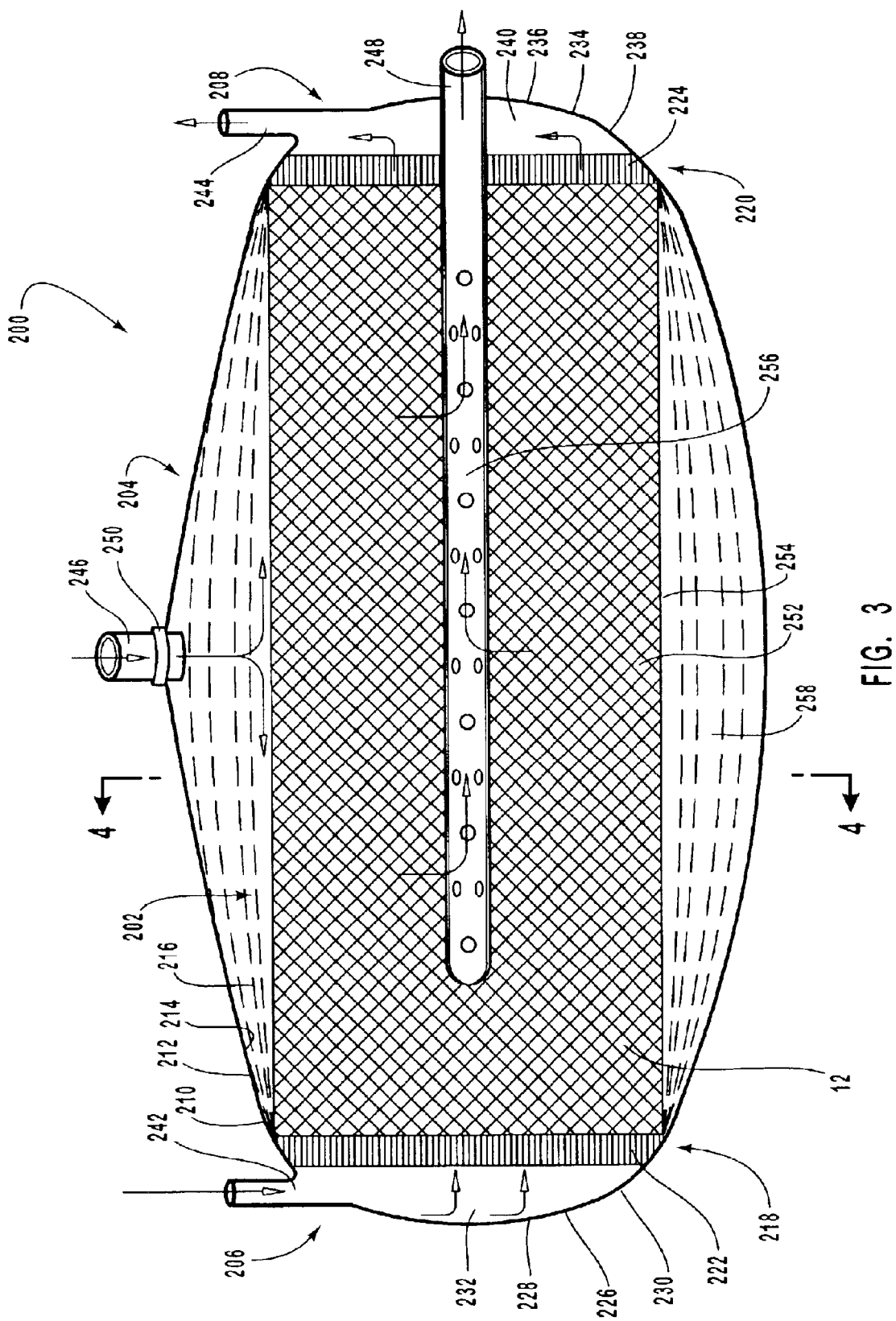
FIG. 3 is a front elevational view of a compliant blood gas exchanger in accordance with another alternative embodiment of the present invention.

The present invention is directed to methods, apparatuses, and applications of a compliant blood gas exchange device using a plurality of hollow fibers to promote blood gas exchange. Hollow fiber technology is based on gas exchange membrane technology. Hollow fibers have been designed which are effective in blood-on-the-outside, gas-on-the-inside applications. In other words, the hollow fibers are selective for gas molecule exchange through the hollow fiber surface or membrane, but simultaneously prevent blood molecule exchange across the membrane. Thus, hollow fibers are ideal for cardiopulmonary studies in which efficient methods for oxygenating the blood system is a constant challenge and new methods for improvement are lacking. One example of the use of hollow fibers for blood gas exchange is described in detail in U.S. patent application Ser. No. 09/935,411, filed Aug. 23, 2001, which is hereby incorporated by reference in its entirety.

In one embodiment of the present invention, the hollow fibers may be housed in an elastomeric sleeve to form a compliant blood gas exchanger. In another embodiment, an elastomeric housing having disposed therein a plurality of hollow fibers is placed adjacent to a chamber. This assembly can then be positioned in a rigid housing to form a heart/lung blood gas exchanger. The elastomeric housing and/or chamber can be connected to a pumping mechanism to form a pulsatile heart/lung blood gas exchanger. In another embodiment, the hollow fibers may be disposed within a rigid container to be used in conjunction with a pumping mechanism to form a more simplified heart/lung blood gas exchanger. Each of these embodiments will now be discussed as well as reference to potential cardiopulmonary uses both inside and outside of the body.

Compliant Blood Gas Exchanger

The present invention incorporates hollow fiber technology as the functioning gas exchange mechanism with blood-on-the-outside and gas-on-the-inside of coated microporous hollow fibers. While a preferred embodiment of the invention concerns blood gas exchange, the present invention is not limited to blood and oxygen as the only liquid and/or gas which can be used in the system.

Turning now to FIG. 1, there is shown a compliant blood gas exchanger 100 in accordance with the present invention. Compliant blood gas exchanger 100 comprises a hollow fiber assembly 102 disposed within a housing 104. Housing 104 has a first end 106, a second end 108, and a sleeve or sidewall 110 extending there between. Sidewall 110 has an exterior surface 112 and an interior surface 114, the interior surface bounding a chamber 116. Compliant blood gas exchanger 100 terminates at first end 106 in a first end cap 126. Similarly, second end 108 of compliant blood gas exchanger terminates in a second end cap 134.

Hollow fiber assembly 102 has a first end 118 and a second end 120. A first mounting collar 122 is disposed at first end 118 and a second mounting collar 124 disposed at second end 120. Hollow fiber assembly 102 also includes a plurality of hollow fibers 12 extending between first mounting collar 122 and second mounting collar 124. The hollow fibers 12 serve the dual function of providing oxygen to chamber 116 and removing carbon dioxide from chamber 116.

First end cap 126 secured at first end 106 is a substantially cup-shaped structure having a first flat portion 128 and a first lip portion 130 formed integrally together. First lip portion 130 receives at least a portion of first mounting collar 122 such that the ends of hollow fibers 12 are in communication with a first gas chamber 132 formed therein. Second end cap 128 secured at second end 108 has a second flat portion 136 and a second lip portion 138 formed integrally together. Second end cap 134 forms a second gas chamber 140 with second mounting collar 124; the ends of hollow fibers 12 being in communication with second gas chamber 140.

Mounting collars 122, 124 are support members which hold the ends of the hollow fibers 12. As such, mounting collars 122, 124 surround the ends of hollow fibers 12 and form an airtight enclosure around the ends of the hollow fibers 12 to prevent the escape of gas into the chamber 116 which could cause foaming and/or a potentially fatal air embolism. Thus, hollow fiber assembly 102 is an air-tight assembly. The ends of the hollow fibers 12 are bound by a potting agent that forms at least a portion of the airtight enclosure around the ends of the hollow fibers. The potting agent may be constructed from polyurethane, but other suitable types of materials such as epoxies, silicones, resins, etc. can also be used. As discussed above, mounting collars 122, 124 of hollow fiber assembly 102 are also in airtight connection with end caps 126, 134. End caps 126, 134 are, in turn, in communication with a gas inlet 142 and a gas outlet 144, respectively. Gas inlet 142 is connected to a gas source (not shown) and gas outlet 144 is connected to a vacuum or other exhaust system (not shown). Thus, a gas flow circuit is created by gas inlet 142, gas outlet 144, end caps 126, 134 and hollow fibers 12.

Centrally disposed through first end cap 126 and first mounting collar 122 is a blood inlet 146. Blood inlet 146 is in communication with chamber 116. Centrally disposed through second end cap 134 and second mounting collar 124 is a blood outlet 148. Blood outlet 148 is also in communication with chamber 116. As shown in FIG. 2C, hollow fibers 12 do not overlap blood inlet 146; rather, hollow fibers 12 are positioned around blood inlet 146 so as to allow blood to flow into chamber 116 among hollow fibers 12. Blood inlet 146 and blood outlet 148 are connected to a blood source (not shown). Blood inlet 146 and blood outlet 148 are in blood-tight communication with chamber 116 such that blood does not escape into end caps 126, 134, mounting collars 122, 124, and/or hollow fibers 12. A blood flow circuit is thus created by blood inlet 146, blood outlet 148, and chamber 116. As such, the gas flow circuit and the blood flow circuit are completely separated from each other by mounting collars 122, 124 and the walls of hollow fibers 12 which will be explained in more detail hereinafter.

In order to maintain the blood flow circuit in blood-tight communication, sidewall 110 must be securely connected to housing 104. In one embodiment, shown in FIG. 1, sidewall 110 may be securely connected to mounting collars 122, 124. In another embodiment, sidewall 110 may be securely connected to end caps 126, 134. In yet another embodiment, sidewall 110 may be securely connected between the mounting collars 122, 124 and end caps 126, 134. Alternatively, sidewall 110 may substantially enclose end caps 126, 134 except for openings for the gas and blood inlets and gas and blood outlets so as to form a substantially enclosed system. In any embodiment, it is important that the seal around sidewall 110 be blood-tight. As such, housing 104 provides protection from leakage of blood outside chamber 116. While FIG. 1 shows housing 104 in distinct parts, housing 104 may be formed integrally or in fewer or more parts without departing from the scope of the present invention. The various parts of housing 104 can be secured together by mechanical means such as welding, injection molding, threading, adhesive, heat sealing, and the like.

The operation of hollow fibers 12 will now be discussed in detail. The surface of hollow fibers 12 provides a means for blood gas exchange between the gas flow circuit and the blood flow circuit in compliant blood gas exchanger 100. Hollow fibers 12 are configured in such a manner so as to maximize the amount of blood gas exchange. In the embodiment shown in FIG. 1, hollow fibers 12 are crimped. The term crimped, as used herein, refers to a configuration in which the hollow fibers are bent or shaped in such as way so as to cause the hollow fibers to become wavy or bent. When hollow fibers 12 are crimped, it increases the disturbance of the blood flow pattern so that more blood comes in contact with hollow fibers 12. Furthermore, it places the hollow fibers 12 such that blood contacts at least a portion of hollow fibers 12 in a substantially transverse direction so as to maximize the gas exchange across hollow fibers 12.

In one embodiment, hollow fibers 12 also comprise a series of segments 150 having an expanded portion 152 and a narrow portion 154 on each side of the expanded portion. Segments 150 may be formed by placing a band (not shown) at each narrow portion 154 to hold the hollow fibers in closer confinement at the narrow portion than at the expanded portion. The degree of constriction may be increased or decreased according to the needs of the patient. The selected configuration should provide a disturbed flow pattern which allows the blood to mix and make repeated contact with the outer surfaces of the hollow fibers 12, creating extensive mixing and secondary flows but without significant obstruction to forward blood flow. Crimping and segmenting the hollow fibers 12 are but some of the methods of maximizing the amount of contact that the blood has with the hollow fibers; other configurations for maximizing the mixing and flow of blood will be discussed hereinafter.

Sidewall 110 may also be configured so as to maximize the mixing and blood flow through chamber 116. In the embodiment shown in FIG. 1, sidewall 110 is shaped to form segments 150 with or without bands to form narrow portions 154. Sidewall 110 is shown resting at least partially against hollow fibers 12. Alternatively, sidewall 110 may be spaced apart from hollow fibers 12. The additional contouring of sidewall 110 prevents stagnation areas from developing and contributes to the mixing of the blood.

Reference is now made to FIGS. 2A through 2C which show various cross-sectional views of the compliant blood gas exchanger 100. While FIGS. 2A through 2C show housing 104 having a substantially circular cross section, various other configurations may be suitable. FIG. 2A is illustrative of the expanded portion 152 of segments 150. The expanded portion 152 allows the hollow fibers 12 to be distanced somewhat from each other. This encourages mixing in the blood flow through chamber 116. FIG. 2B shows the narrow portion 154 of a segment 150. As shown, the hollow fibers 12 are more compact, thus serving to restrict blood flow through chamber 116 to create more mixing.

Finally, FIG. 2C shows the ends of hollow fibers 12 fixed in position by mounting collar 124. Blood outlet 148 is also shown disposed through the center of mounting collar 124.

As shown in FIGS. 2A through 2C, hollow fibers 12 are generally positioned adjacent to or proximate neighboring hollow fibers. Hollow fibers 12 may form a generally contiguous structure and/or a distance may separate the fibers. In the latter embodiment, hollow fibers 12 are separated by a distance such that the fibers do not significantly increase the resistance to blood flow within the device. In one embodiment, the hollow fibers 12 are positioned such that a generally constant distance separates the hollow fibers to promote uniform interaction of the blood and the fibers, which provides for better mixing of the blood and increased gas exchange rates as illustrated in FIGS. 2A through 2C. The hollow fibers 12 may also be maintained in a spaced relationship to maximize the surface area of the fibers that is in contact with the blood and to more uniformly distribute the blood flow over the fibers.

In an alternative embodiment, hollow fiber assembly 102 may have generally conical-shaped hollow fiber segments. For example, means may be provided to maintain hollow fibers 12 in segments 14 such that the hollow fibers extend radially in the expanded region of each segment. The radial configuration of hollow fibers 12 provides that blood will flow into blood inlet 146 and flow transversely and/or tangentially over most of the length of hollow fibers 12. This flow pattern increases gas exchange capability of compliant blood gas exchanger 100. Advantageously, by positioning the generally conical-shaped hollow fiber segments 14 at up to a right angle with respect to the blood flow, that increases the rate of gas exchange and provides better mixing of the blood during the interaction of the blood with the fibers 12. Significantly, decreasing or eliminating stagnation areas and boundary layers effectively provides increased surface area for gas exchange.

In one embodiment, the generally conical-shaped hollow fiber segments 14 extend radially outwardly from a central axis at an angle of at least 30°. In another embodiment, segments 14 extend radially outwardly from a central axis at an angle of at least 45°. Desirably, the generally conical-shaped hollow fiber segments 14 extend from a central axis at an angle of up to 90° such that the blood flow impacts the fibers at a relatively sharp or acute angle. Significantly, the impact of the blood flow at an acute angle provides more direct contact of the blood with the fibers, which increases the gas exchange rates. Additionally, this acute angle of impact results in better mixing of the blood and helps eliminate stagnation areas where the blood and fibers do not interact. This acute angle of impact also helps prevent a boundary layer from developing, which limits the exchange of gas. Further, the acute angle of impact of the blood flow with the fibers creates more secondary blood flow, which also increases the gas exchange rate. Other methods may be used to form hollow fibers 12 and/or segments 150; the present invention is not limited to the aforementioned examples.

In the embodiment of FIG. 1, sidewall 110 is constructed of an elastomeric material. The term elastomeric as used herein refers to a material which, when distended, is biased toward a nondistended position. The sidewall 110 may distend away or toward hollow fibers 12. Because of the elastomeric nature of sidewall 110, chamber 116 may expand or contract depending on internal or external pressures. This is advantageous when compliant blood gas exchanger 100 is used intracorporeally because it has been shown that a rigid housing causes a high systolic blood pressure. Having an elastomeric sidewall 110 which is compliant with the pulsatile pressures from the patient's left or right ventricles decreases the risk of high blood pressure and creates a system more physiologically compatible with the patient.

The thickness of sidewall 110 may vary depending on the needs of the patient. For example, a weaker heartbeat in an infant may require less strength than a stronger heartbeat in an adult. It will be appreciated that a thicker elastomeric material is less distensable than a thinner elastomeric material. Accordingly, the thickness of sidewall 110 should be selected to provide an optimal distension depending on the size of housing 102 and the size of the patient. In one embodiment, sidewall 110 may have a thickness of about 2 to about 5 micrometers. In another embodiment, sidewall 110 has a thickness of about 0.5 to about 1 micrometer.

The elastomeric portion of sidewall 110 can be formed from any suitable elastomer such as polyurethane, polyvinyl chloride, silicone, rubber, or the like. In one embodiment, end caps 126, 134 are formed from a rigid material which can be any suitable material such as polyurethane, polyethylene, or other plastic material. In another embodiment, all parts of housing 104 are constructed from a biocompatible material and coated with a siloxane, fluorinated polyurethane, or other state-of-the-art polymer. The material used to form sidewall 110 and end caps 126, 134 may be transparent so that the interior workings of the device may be viewed.

Each hollow fiber 12 is constructed from a biocompatible material such as polypropylene or other state-of-the-art polymer. Another suitable material for constructing hollow fiber 12 is polyethylene. Other suitable biocompatible materials may be used to construct the hollow fibers 12, such as polyurethane, polyvinyl chloride, silicone and the like. Additionally, the hollow fibers 12 have a microporous structure to facilitate the diffusion of gas through the walls of the fibers.

In one embodiment, hollow fibers 12 include a membrane. The term "membrane" as used herein, refers to a thin, gas permeable coating which allows gas exchange to occur in an out of the surface of hollow fibers 12. The membrane enhances the exchange of gas in and out of the blood. Because of the thinness of the membrane, the membrane is not shown in the accompanying drawings. The membrane may include a siloxane, fluorinated polymer, or the like, with a thickness of approximately 0.1 micron to 0.5 micron to. Other suitable types of coatings may also be used depending upon the particular use of the hollow fibers 12.

Additionally, the membrane may include a substance that minimizes thrombosis formation. Because the hollow fibers 12 are in contact with flowing blood, it is desirable to minimize thrombosis formulation. Accordingly, the hollow fibers 12 may be coated with membrane comprising thrombo-resistant material such as siloxane. In addition, the membrane may comprise a non-leachable, permanent covalently-bonded thromboresistant and blood compatible coating containing anti-thrombin material, such as heparin. It will be appreciated that the terms "membrane" and "coating" may be used interchangeably throughout this specification and claims to indicate that the hollow fibers 12 are coated with a membrane as defined above.

Gas inlet 142, gas outlet 144, blood inlet 146, and blood outlet 148 may be connected to corresponding conduits (not shown in FIG. 1). It will be appreciated that any inlet or outlet disclosed in the present invention may be connected to a corresponding conduit. The conduits may be constructed of a biocompatible material such as polyethane or polyethylene tubes. It will be appreciated that the designations of blood inlet, blood outlet, gas inlet and gas outlet are for description purposes only and not intended to be limiting to the scope of the present invention. For example, while the term gas inlet may designate the inflow of gas, the gas inlet may serve equally well as a gas outlet if the flow of gas is reversed in the device. Similarly, it may be advantageous to reverse the flow of blood having the blood flow into the blood outlet and out of the blood inlet.

The foregoing describes a unitary, self-contained blood gas exchange system in which the compliant blood gas exchanger 100 provides blood gas exchange between the gas flow circuit and the blood flow circuit. In operation, oxygen rich gas flows through gas inlet 142, into first end cap 126 and into hollow fibers 12. The gas flows through the microconduits (i.e., lumens) formed by hollow fibers 12. The coated surface of hollow fibers 12 allows gas molecules to be exchanged but prevents blood molecules from entering. Venous (i.e., oxygen-deficient) blood is introduced into blood inlet 146 and into chamber 116. As the blood flows in a disturbed pattern through chamber 116, oxygen exchange occurs through the walls of hollow fibers 12. Simultaneously, carbon dioxide exchange is encouraged because of the partial pressure gradient across the coated surface of hollow fibers 12. Carbon dioxide enters hollow fibers 12 and exits out of second end cap 134 and out gas outlet 144. Similarly, arterial (i.e., oxygen-rich) blood exits out blood outlet 148 and into the blood stream.

Compliant blood gas exchanger 100 may operate at subatmospheric pressures. In particular, oxygen-enriched gas (preferably nearly 100% oxygen) is introduced into the gas inlet 142 at about atmospheric, or slightly above atmospheric, pressure. A vacuum (not shown) is attached to the gas outlet 144 to provide the necessary pressure difference to cause the oxygen gas to flow through the hollow fibers 12. The oxygen gas experiences a pressure drop as it flows through the gas inlet 142 towards the hollow fibers 12. As a result, the pressure of the oxygen gas as it enters the hollow fibers 12 is subatmospheric.

Operation of the compliant blood gas exchanger 100 at low pressure will enhance carbon dioxide removal, while providing adequate blood gas exchange. The driving force behind blood gas exchange is the difference between the partial pressures of the oxygen and carbon dioxide in the blood stream and the partial pressures of the oxygen and carbon dioxide in the hollow fibers 12. Lowering the pressure within the hollow fibers 12 necessarily promotes exchange of carbon dioxide from the blood into the fibers. Advantageously, because nearly pure oxygen is supplied to compliant blood gas exchanger 100, the partial pressure of oxygen is sufficiently high to achieve adequate blood gas exchange.

Traditionally, blood gas exchange has been the primary goal in patients suffering from acute respiratory failure. It is also well known that removal of carbon dioxide from blood is equally important. Thus, operation of the compliant blood gas exchanger 100 at subatmospheric pressures enhances the overall effectiveness of the device. Moreover, because the operating pressure, in one embodiment, is less than the blood pressure, any leak in the compliant blood gas exchanger 100 cannot introduce air bubbles within the blood stream. Any such leak would introduce blood within the hollow fibers 12, sealing the leak, rather than allowing gas to enter the blood stream. Therefore, operation of the compliant blood gas exchanger 100 at subatmospheric pressures provides significant safety benefits.

While the disclosed invention is capable of reproduction in a wide variety of forms and specific embodiments, by way of example, some of the specifications of two embodiments of the present invention will now be set forth. In one embodiment 12,000 hollow fibers 12 are bundled together. Hollow fibers 12 are about 40 to 60 cm long with an inner diameter of about 120 microns and an outer diameter of about 170 microns. The pore size is about 0.03 to 0.05 microns, with a porosity of about 70%. This results in about 3.0 $m^2$ of gas exchange surface area. A compliant blood gas exchanger 100 having these specifications and having a blood flow rate of about 5 to 8 L/min has been shown to result in 300 ml/min or more of $O_2$ and $CO_2$ gas exchange, respectively, under normal operating conditions.

In another embodiment, about 10,000 to about 15,000 hollow fibers 12 are bound together. Hollow fibers are about 40 cm to 60 cm long with an inner diameter of about 120 to 190 microns and an outer diameter of about 170 to 240 microns. The volumetric packing density of the hollow fibers within chamber 116 is about 18 to 22%. The pore size on the surface of the hollow fibers is about 0.03 to 0.05 microns, with a porosity of about 70%. This results in about 1.5 to 2.0 $m^2$ of gas exchange surface area with the ability to exchange about 200 ml/min $O_2$ and $CO_2$ under normal operating conditions.

As shown in FIG. 1, hollow fiber assembly 102 has five segments 105. However, more or less segments 150 may be employed. The length and diameter of the hollow fibers 12 may also be larger or smaller depending, for example, upon the intended use of the compliant blood gas exchanger 100. Because the amount of gas exchange required will depend upon the size and condition of the patient, the number of hollow fibers 12 may be varied. For example, compliant blood gas exchanger 100 for use with an infant may only have about 1000 hollow fibers while an adult may require 15,000 or more hollow fibers to provide adequate blood gas exchange. Similarly, the size and length of the fibers could be varied according to the amount of gas to be exchanged. Thus, the hollow fibers can be sized and configured to fit within different sized housing, such as for a youth or adult patient allowing compliant blood gas exchanger 100 to be used in locations of various sizes and configurations.

Another embodiment for compliant blood gas exchanger is shown in FIG. 3. As depicted in FIG. 3, compliant blood gas exchanger 200 comprises a hollow fiber assembly 202 disposed within a housing 204. Housing 204 has a first end 206, a second end 208, and a sidewall 210 extending there between. Sidewall 210 has an exterior surface 212 and an interior surface 214, the interior surface bounding a chamber 216. Compliant blood gas exchanger 200 terminates at first end 206 in a first end cap 226. Similarly, second end 208 of compliant blood gas exchanger 200 terminates in a second end cap 234.

Hollow fiber assembly 202 has a first end 218 and a second end 220. Hollow fiber assembly 202 comprises a first mounting collar 222 and a second mounting collar 224 at first end 218 and second end 220, respectively, of hollow fiber assembly 202. Hollow fiber assembly 202 also includes a plurality of hollow fibers 12 extending between first mounting collar 222 and second mounting collar 224.

First end cap 226 is secured at first end 206 of compliant blood gas exchanger 200 and is a substantially cup-shaped structure having a first flat portion 228 and a first lip portion 230 formed integrally together. First lip portion 230 receives at least a portion of first mounting collar 222 such that the ends of hollow fibers 12 are in communication with a first gas chamber 232 formed therein. Second end cap 234 has a second flat portion 236 and a second lip portion 238 formed integrally with each other. Second end cap 234 forms a second gas chamber 240 with second mounting collar 224.

Mounting collars 222, 224 surround the ends of hollow fibers 12 and are in airtight connection with first end cap 226 and a second end cap 234, respectively. End caps 226, 234 are, in turn, in communication with a gas inlet 242 and a gas outlet 244, respectively. Thus, a gas flow circuit is created by gas inlet 242, gas outlet 244, end caps 226, 234, and hollow fibers 12. Disposed substantially transversely through sidewall 210 and into chamber 216 is a blood inlet 246. A reinforcing collar 250 is disposed around blood inlet 246. Centrally disposed through second end cap 234 and second mounting collar 224 is a blood outlet 248. Blood outlet 248 is also in communication with chamber 216. Blood inlet 246 and blood outlet 248 are in blood-tight communication with chamber 216 such that blood does not escape into end cap 226, 234 or outside of sidewall 210. Thus, a blood flow circuit is created by blood inlet 246, blood outlet 248 and chamber 216.

Sidewall 210 is securely connected to mounting collars 222, 224 and/or end caps 226, 234 to form a blood-tight seal. The various parts of housing 204 can be secured together by mechanical means such as welding, injection molding, threading, adhesive, heat sealing, and the like.

Figure 4:
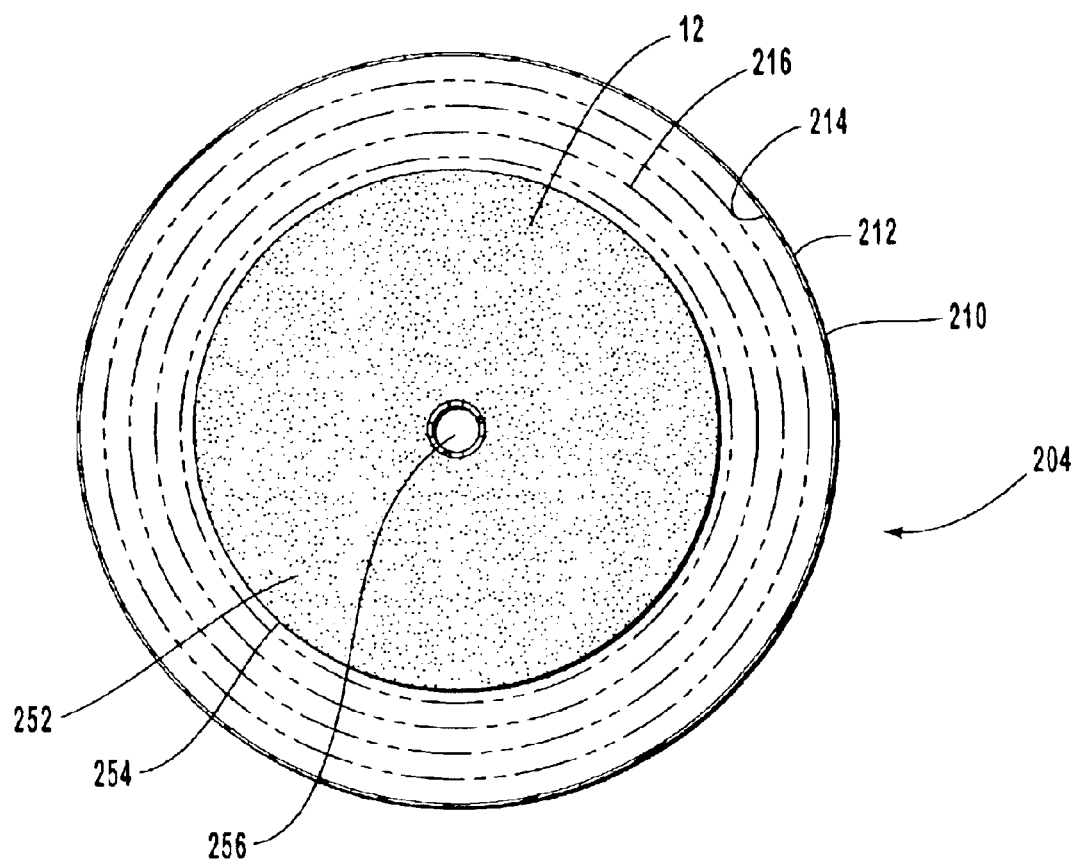
FIG. 4 is a cross-sectional view of the compliant blood gas exchanger shown in FIG. 3 taken along line 4—4.

Hollow fibers 12 are configured so as to maximize the gas exchange across the hollow fiber membrane. In the embodiment shown in FIG. 3, hollow fibers 12 are woven into a pattern similar to that described in U.S. Pat. No. 5,230,862, incorporated herein by specific reference. In essence, hollow fibers 12 are of two sizes which are interwoven together to form a matrix 252. Hollow fibers 12 are woven such that they are generally evenly dispersed throughout matrix 252. The dual size hollow fiber arrangement having this weaving pattern serves to maximize the surface area of the fibers that is in contact with the blood and to more uniformly mix the blood flow over the fibers. There a number of different weaving patterns that may be employed to optimize the blood gas exchange. As shown in FIG. 4, matrix 252 has a substantially cylindrical configuration having a boundary 254. A channel 256 is centrally disposed within matrix 252. Channel 256 is in communication with blood outlet 248, which purpose will be described in more detail hereinafter.

In the embodiment of FIG. 3, sidewall 210 is constructed of an elastomeric material. Because of the elastomeric nature of sidewall 210, chamber 216 may expand or contract depending on internal or external pressures as shown by the phantom lines in FIGS. 3 and 4. When a volume of blood is introduced into chamber 216, sidewall 210 distends, creating a reserve 258 around matrix 252. FIGS. 3 and 4 show sidewall 210 moving away from boundary 254 as the pressure increases within chamber 216.

The blood flow circuit and gas flow circuit operate substantially similar to that described for compliant blood gas exchanger 100 shown in FIG. 1. The woven pattern of hollow fibers 12 and the elastomeric qualities of sidewall 210 advantageously assist in an optimal blood flow pattern throughout matrix 252. During operation, blood infuses into chamber 216 through blood inlet 246. Sidewall 210 distends as the pressure is received by chamber 216. When sidewall 210 distends, reserve 258 expands to hold the excess amount of blood. The elasticity of sidewall 210 causes it to bias back into its original position. Such action forces the blood in reserve 258 to flow substantially perpendicularly through matrix 252 and to be collected centrally through channel 256. The blood flows through channel 256 and out blood outlet 248. This particular blood flow pattern is desirable because it allows the blood to contact the hollow fibers 12 at a substantially transverse angle.

Blood inlet 246 and blood outlet 248 are positioned such that in one embodiment, venous blood may enter the periphery and exit the center. In another embodiment, arterial blood may enter the center and exit the periphery. This may be advantageous, for example, to allow the surgeon to position the compliant blood gas exchanger such that it occupies the least amount of space and conduit material.

The specifications of one embodiment of compliant blood gas exchanger 200 will now be set forth. In one embodiment, about 12,000 hollow fibers were used to create matrix 252 having lengths of about 40 cm. Two sizes of hollow fibers were woven together having inner diameters of about 120 microns and about 190 microns. Thus, about 2.9 $m^2$ of gas exchange surface area is provided. A compliant blood gas exchanger 200 having these specifications and having a blood flow rate of about 5 to 8 L/min has been shown to exchange more than 280 ml/min of $O_2$ and $CO_2$, respectively.

In another embodiment, compliant blood gas exchanger 200 comprises 30,000 hollow fibers having lengths of about 26 cm. Hollow fibers 12 were woven together with two sizes of hollow fibers having inner diameters of about 120 microns and 190 microns. This provides about 4.4 $m^2$ of gas exchange surface area. Such a device having these specifications and under a blood flow rate of about 6 to 10 L/min has been shown to exchange more than 400 ml/min of $O_2$ and $CO_2$.

It will be appreciated that the dimensions of the hollow fibers, surface area of the hollow fibers exposed to blood, packing density of the hollow fiber bundles, and the size and configuration for the blood and gas inlets and outlets may be modified in order to achieve optimum performance depending on the size of the patient and the location of the device in relation to the patient's body.

Intrathoracic Blood Gas Exchanger

When inside the body, the compliant blood gas exchanger 100 or 200 may be implanted as an artificial respiratory prosthesis. In one embodiment, the compliant blood gas exchanger can be used as an implantable intrathoracic artificial lung. In this embodiment, the compliant blood gas exchanger provides all the blood gas exchange requirements for a human having irreversible, end-stage respiratory failure. It should be emphasized that even though the compliant blood gas exchanger can provide all the blood gas exchange requirements of failing natural lungs, it is necessary that some of the patient's lung remain in the patient's body. The lung is an essential organ for regulating chemical activity in the body. For example, the lung plays a part in regulating enzyme production, regulating blood pressure and regulating thyroid function. This can be accomplished by conducting a pneumonectomy (an operation to remove part of or the entire lung) on, for example, the right lung and leaving intact the left lung. After one natural lung is removed, and the compliant blood gas exchanger implanted, the blood flow to the remaining lung is severely restricted, forcing a majority of the venous blood to flow into the intrathoracic artificial lung. In one embodiment, after the compliant blood gas exchanger is implanted, 70 percent of the right ventricular (venous) blood flow is directed into the blood gas exchanger leaving 30 percent going to the remaining natural lung. In another embodiment, 90 percent of the venous blood flow is directed to the blood gas exchanger while the remaining natural lung receives only 10 percent.

Figure 5:
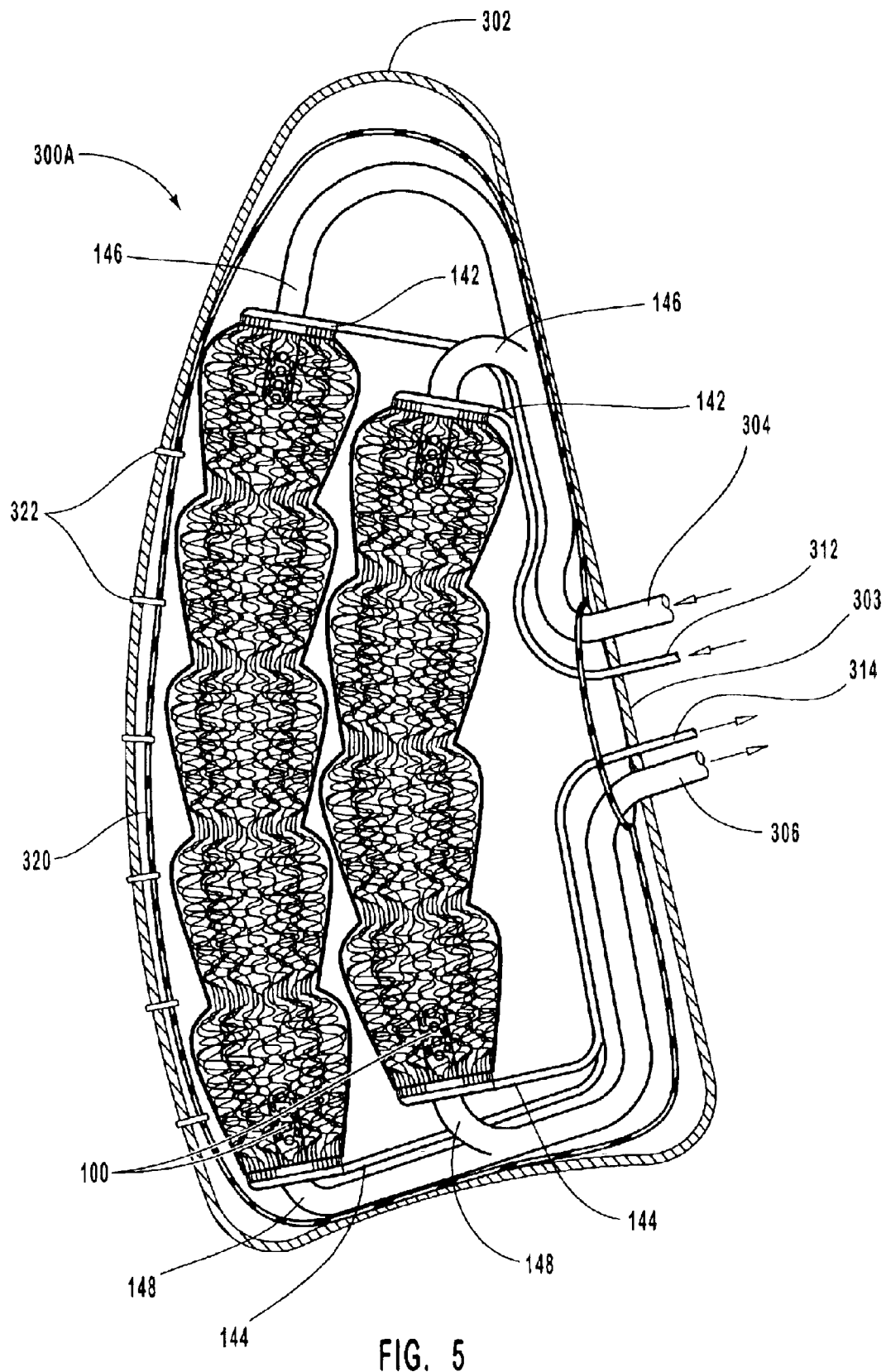
FIG. 5 is a front elevational view of a compliant blood gas exchange system as an implantable artificial lung application of the present invention, illustrating two compliant blood gas exchangers attached in parallel.

As shown in FIG. 5, a blood gas exchange system 300A comprises at least one compliant blood gas exchanger 100 being implanted into a thoracic cavity 302 after a pneumonectomy. The compliant blood gas exchanger 100 is similar to the embodiment described with regard to FIGS. 1 and 2A–2C. As such, the details of compliant blood gas exchanger 100 will not be repeated and the similar features will be referred to with like reference numbers. It will be appreciated that compliant blood gas exchanger 200 would serve equally as well, but for ease of reference, the following discussion will be limited to compliant blood gas exchanger 100.

As shown in FIG. 5, two compliant blood gas exchangers 100 are shown in parallel. In one embodiment, a compliant blood gas exchanger 100 having five segments is connected in parallel with a compliant blood gas exchanger 100 having four segments. The number and sizes of compliant blood gas exchangers may vary depending on the needs of the patient. The compliant blood gas exchangers 100 are implanted into the thoracic cavity 302 after a complete pneumonectomy.

FIG. 5 shows blood gas exchange system 300A having a blood inlet conduit 304 and a blood outlet conduit 306. Blood inlet conduit 304 and blood outlet conduit 306 each branch out into one or more subconduits which are connected to their respective blood inlet 146 or blood outlet 148 of each compliant blood gas exchanger 100. Accordingly, more than two compliant blood gas exchangers 100 may be profitably employed.

Blood gas exchange system 300A also has a gas inlet conduit 312 and a gas outlet conduit 314. Gas inlet conduit 312 and gas outlet conduit 314 each branch out into one or more subconduits which are connected to their respective gas inlets 142 or gas outlets 144 of each compliant blood gas exchanger 100.

During implantation, a vascular graft is constructed from the pulmonary artery leaving the right ventricle to the blood inlet conduit 304. Similarly, a vascular graft is surgically formed between the blood outlet conduit 306 and a pulmonary vein entering the left atrium. Thus, right ventricular (venous) blood is brought into the compliant blood gas exchangers, which oxygenates the blood and removes carbon dioxide, and arterial blood is returned to the left atrium of the heart. In this manner, the heart and the compliant blood gas exchangers 100 form a continuous cardiopulmonary circuit once supplied by the removed natural lung.

In an alternative embodiment, blood inlet conduit 304 of the compliant blood gas exchanger 100 may be vascularly grafted to the superior vena cava or inferior vena cava which enters the right atrium. The blood outlet conduit 306 would simultaneously be grafted to an aortic branch to deliver poorly oxygenated blood to compliant blood gas exchanger 100. Various medically accepted vascular configurations for implanting compliant blood gas exchangers 100 or 200 may be applied depending on the blood gas exchange needs of the patient. For example, a patient requiring a compliant blood gas exchanger to provide almost total blood gas exchange may require the first vascular configuration while a patient requiring less blood gas exchange may only require the second vascular configuration.

In operation, gas inlet 142 is connected to an oxygen source and gas outlet 144 is connected to an exhaust system such that oxygen is introduced at subatmospheric pressure. Venous blood is pumped by the heart into compliant blood gas exchangers 100 where oxygen is exchanged through the walls of hollow fibers 12. At the same time, carbon dioxide is exchanged in chamber 116. Having thus been oxygenated and stripped of carbon dioxide, arterial blood exits compliant blood gas exchangers 100 and is delivered to the body. Because compliant blood gas exchangers 100 have an elastomeric sidewall 110, the unit is able to respond to the systolic and diastolic pressures created by the heart. The blood gas exchange system 300A shown in FIG. 5 has functioned in vivo for up to six weeks without deterioration of gas exchange, without harmful accumulation of thrombus, and without release of systemic gross or microscopic thromboemboli.

In one embodiment, compliant blood gas exchangers 100 are disposed in a pouch 320 shaped to fit within the thoracic cavity 302. Pouch 320 substantially surrounds compliant blood gas exchangers 100, leaving an opening 303 for the blood and gas conduits. Pouch 320 is provided to maintain the compliant blood gas exchangers 100 in their relative positions within the thoracic cavity 302. Pouch 320 also prevents water from forming in the thoracic cavity, which would eventually push the compliant blood gas exchangers toward the dependent portions of the thoracic cavity. In one embodiment, pouch 320 is transparent and is made of an elastomeric, biocompatible material such as polyurethane. Pouch 320 is attached to the walls of the thoracic cavity 302 by a series of fasteners 322. Fasteners 322 may be any medically acceptable structure such as sutures or staples.

In one embodiment, two compliant blood gas exchangers 100 are connected in parallel. Each compliant blood gas exchanger 100 has approximately 6000 hollow fibers 12. This results in about 3.0 m$^2$ of gas exchange membrane which will exchange about 300 ml/min of $O_2$ and $CO_2$ at blood flow rates of about 4 to 6 L/min. Resistance to blood flow is less than 15 torr at a blood flow rate of 5 L/min.

In another embodiment, two compliant blood gas exchangers 100 are connected in parallel. Each compliant blood gas exchanger comprises approximately 10,000 to 15,000 hollow fibers, a resultant gas exchange membrane surface of about 3.0 to 4.0 m$^2$. These specifications result in at least 400 ml/min of $O_2$ and $CO_2$ exchange at blood flow rates of about 4 to 6 L/min. Resistance to blood flow is less than 15 torr at a blood flow of 5 L/min.

Figure 6:
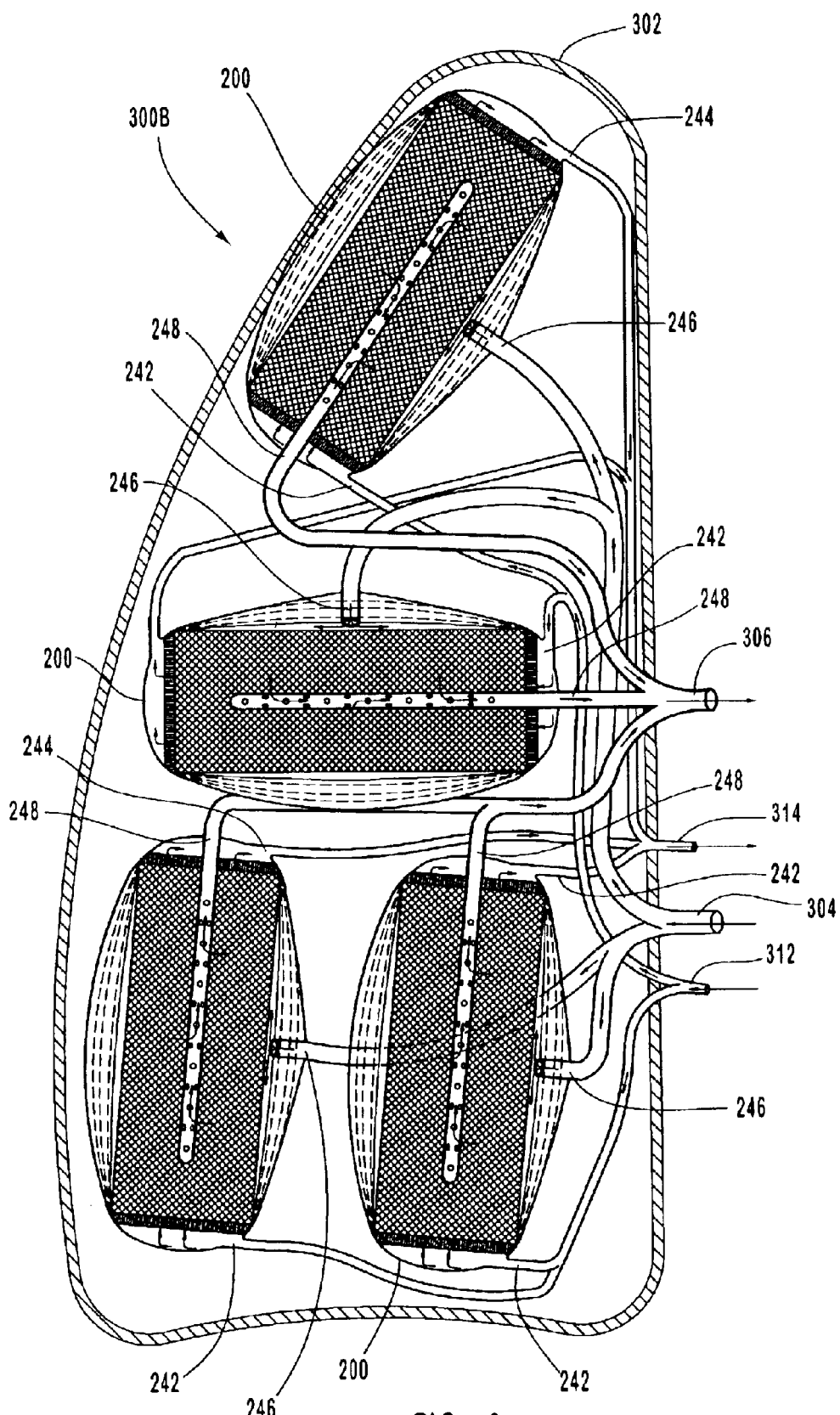
FIG. 6 is a front elevational view of a compliant blood gas exchange system as an implantable artificial lung application of the present invention, illustrating a plurality of compliant blood gas exchangers attached in parallel.

FIG. 6 shows another embodiment of an implantable intrathoracic artificial lung. FIG. 6 depicts a blood gas exchange system 300B comprising a plurality of compliant blood gas exchangers 200 connected in parallel and implanted into the thoracic cavity 302 of a patient. The embodiment depicted in FIG. 6 shows four compliant blood gas exchangers 200 connected in parallel. More or less compliant blood gas exchangers 200 may be used depending on the size and gas exchange requirements of the patient. The compliant blood gas exchanger 200 is similar to the embodiment described with regard to FIGS. 3 and 4. As such, the details of compliant blood gas exchanger 200 will not be repeated and the similar features will be referred to with like reference numbers. It will be appreciated that the compliant blood gas exchanger 100 would serve equally as well, but for ease of reference, the following description will be limited to compliant blood gas exchanger 200.

In the embodiment of FIG. 6, the compliant blood gas exchangers 200 are arranged to be anatomically similar to segments or lobes of a natural lung. That is, the human lung is somewhat pear-shaped with less gas exchange area at the top than at the bottom. Similarly, the compliant blood gas exchangers 200 are arranged so that they increase in number toward the bottom of the thoracic cavity 302.

System 300B has a blood inlet conduit 304 connected to the pulmonary artery by vascular graft (not shown). Blood inlet conduit 304 branches into a number of subconduits connected to the blood inlets 246 of each compliant blood gas exchanger 200. Likewise, a blood outlet conduit 306 is vascularly grafted to the left atrium. The blood outlet conduit 306 branches out into a number of blood outlet subconduits 310 corresponding to the number of blood outlets 248 of compliant blood gas exchangers 100.

System 300B also has a gas inlet conduit 312 and gas outlet conduit 314 branching out into subconduits which are connected to their respective gas inlets 242 and gas outlets 244 of compliant blood gas exchanger 100. During operation, gas inlet conduit 312 and gas outlet conduit 314 are connected to an oxygen source and exhaust system.

It will be appreciated that blood gas exchange system 300B operates substantially similar to the blood gas exchange system 300A and the description of the operation of the compliant blood gas exchangers 200 described above.

In one embodiment, each compliant blood gas exchanger 200 has 7,500 hollow fibers. Two sizes of hollow fibers are used. Each compliant blood gas exchanger 200 is about 12 cm long and about 6 cm in diameter and provides approximately 1.0 m$^2$ of gas exchange surface area to the circulating blood. Thus, four compliant blood gas exchangers 200 exchange more than 400 ml/min of $O_2$ into and 400 ml/min of $CO_2$ out of the blood.

Those skilled in the art will appreciate the potential that compliant blood gas exchangers 100 and 200 have for substantially improving the support of patients with advanced, irreversible respiratory failure. While it is necessary that some of the natural lung tissue remains in the patient for biochemical reasons (unrelated to gas exchange functions), a single blood gas exchange system 300A or 300B can provide the blood gas exchange requirements for an adult person experiencing advanced respiratory illness. Further, all of the blood gas exchange occurs inside the patient, leaving only a small oxygen pump/tank to be extracorporeally transported with the patient allowing a markedly improved and extended quality of life.

AV Shunt

Figure 7:
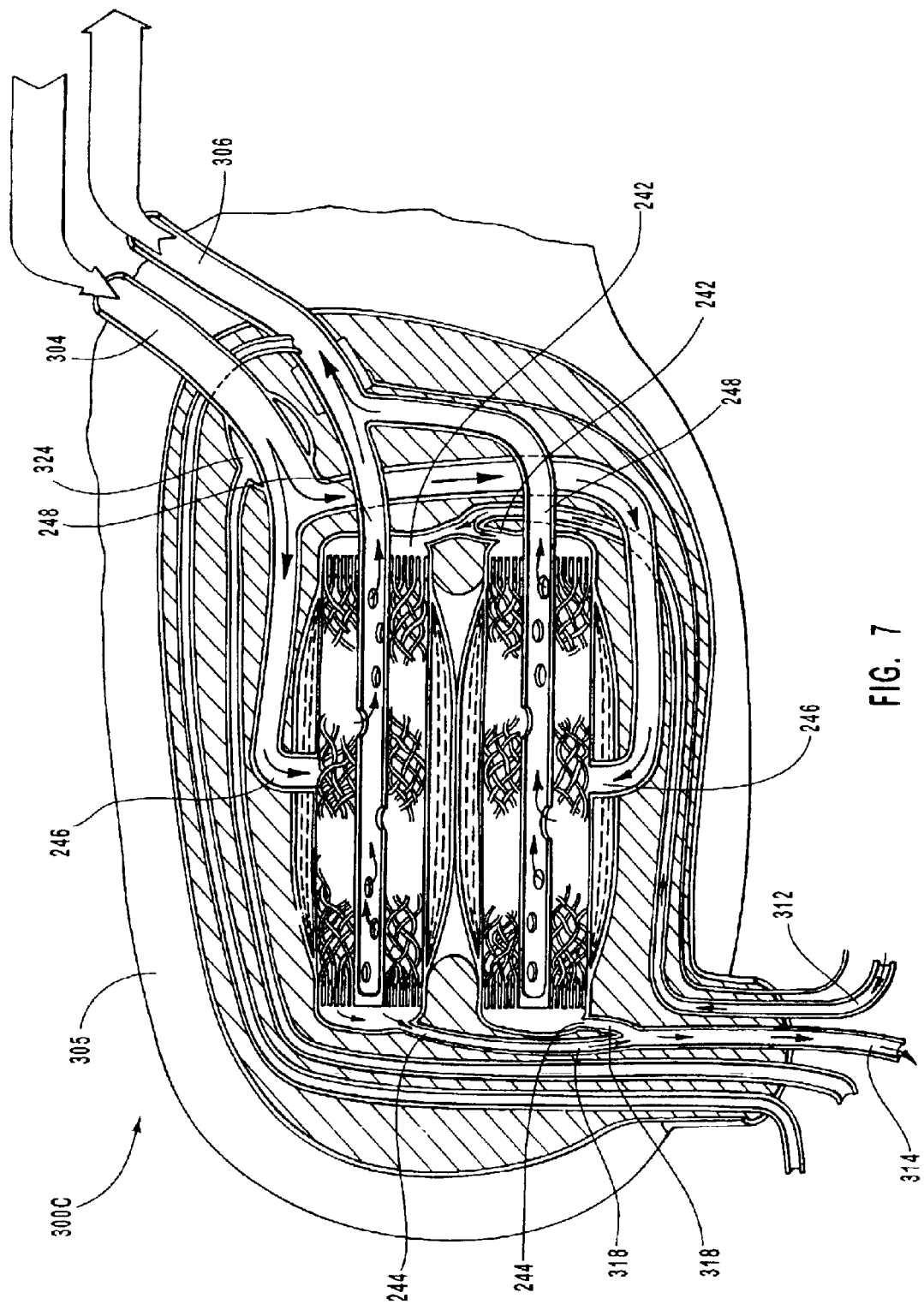
FIG. 7 is a front elevational view of a compliant blood gas exchange system in accordance with another alternative embodiment of the present invention, illustrating two compliant blood gas exchangers attached in parallel to construct a pumpless AV shunt.

Another useful application of compliant blood gas exchanger 100 or 200 is to utilize the device as a pumpless arterio-venous shunt (AV shunt). With reference to FIG. 7, an AV shunt system 300C is shown. AV shunt system 300C is positioned in an area located by a major vein and artery, such as the lower abdomen. One such area 305 in the lower abdomen is shown formed in FIG. 7. AV shunt system 300C comprises two compliant blood gas exchangers 200 placed extraperitoneally in area 305 and connected in parallel. It will also be understood that compliant blood gas exchanger 100 may work equally as well, but for ease of discussion, the follow description will be limited to compliant blood gas exchanger 200.

FIG. 7 shows system 300C having a blood inlet conduit 304 and a blood outlet conduit 306. Blood inlet conduit 304 and blood outlet conduit 306 each branch out into one or more subconduits which are connected to their respective blood inlet 246 or blood outlet 248 of each compliant blood gas exchanger 200. Accordingly, it will be appreciated that more than two compliant blood gas exchangers 200 may be profitably employed. Blood inlet conduit 304 is vascularly grafted to a branch of an artery, such as the iliac or femoral artery. Likewise, the blood outlet conduit 306 is vascularly grafted to a branch of a vein, such as the iliac or femoral vein.

System 300C also has a gas inlet conduit 312 and a gas outlet conduit 314. Gas inlet conduit 312 and gas outlet conduit 314 each branch out into one or more subconduits which are connected to respective gas inlets 242 or gas outlets 244 of each compliant blood gas exchanger 200.

A blood line occluder 324 may be disposed about blood inlet conduit 304. Blood line occluder 324 is operable by a technician to regulate the blood flow through a blood vessel. Blood line occluder 324 is monitored by a vascular pressure gauge. When compliant blood gas exchanger 200 is implanted into the abdominal cavity and the vascular connections made to blood inlet 246 and blood outlet 248, the blood line occluders 324 is adjusted around the artery until the optimal amount of blood flow is reached. It will be appreciated that AV shunt system 300C operates substantially similar to the blood gas exchange system 300A and 300B.

Heart/Lung Blood Gas Exchanger

The expansile chamber of compliant blood gas exchanger 100 or 200 may also be used in conjunction with a rigid outer housing to form a dual-chamber heart/lung blood gas exchanger. That is, a first chamber is placed adjacent to a second chamber such that changes in pressure of the second chamber influence the pressure of the first chamber. A dual-chamber provides a means for creating a pulsatile flow which replicates the pulsatile flow found in the natural cardiopulmonary system. Thus, by positioning the two chambers within a rigid outer housing and applying a pumping mechanism, the compliant blood gas exchanger 100 or 200 may become an integral, automated device useful for a right ventricular or veno arterial extracorporeal membrane oxygenator (ECMO). Alternatively, the compliant blood gas exchanger may be used for a pulsatile flow pump blood gas exchanger which is portable and compact for use in ECMO, cardiopulmonary bypass, or emergency room situations. These and other embodiments will now be described in detail.

Depicted in FIG. 8 is a heart/lung blood gas exchanger 400. Heart/lung blood gas exchanger 400 comprises a hollow fiber assembly 402 disposed in a housing 404. Housing 404 has a first end 406, a second end 408, and an outer sidewall 410 extending there between. Outer sidewall 410 has a first end 412, a second end 414, an exterior surface 416 and an interior surface 418. Interior surface 418 bounds a first chamber 424 as will be described hereinafter in more detail. First end 412 of outer sidewall 410 is formed having a first annular groove 492. Similarly, second end 414 of outer sidewall 410 is shown having a second annular groove 494 formed thereon. Heart/lung blood gas exchanger 400 terminates at first end 406 in a first end cap 420 and terminates at second end 408 in a second end cap 422.

Disposed within housing 404 is hollow fiber assembly 402. Hollow fiber assembly 402 has a first end 426 and second end 428. Hollow fiber assembly 402 comprises a first mounting collar 430 disposed at first end 426, a second mounting collar 432 disposed at second end 428, and a plurality of hollow fibers 12 disposed there between. Mounting collars 430, 432 surround the ends of hollow fibers 12, but do not block the ends of the hollow fibers so as to allow gaseous communication throughout the length of the hollow fibers.

Extending between first end 426 and second end 428 of hollow fiber assembly 402 is an intermediate sidewall 434. Intermediate sidewall 434 has a first end 436, a second end 438, an exterior surface 440 and an interior surface 442.

Interior surface 442 of intermediate sidewall 434 bounds a second chamber 444 which houses hollow fibers 12. Intermediate sidewall 434 also separates second chamber 444 from first chamber 424. Thus, first chamber 424 is bounded by exterior surface 440 of intermediate sidewall 434 and interior surface 418 of outer sidewall 410.

First end cap 420 and second end cap 422 are disposed at first end 406 and second end 408, respectively, of housing 404. First end cap 420 is a substantially cup-shaped structure having a substantially first flat portion 447 and a first lip portion 449 formed integrally from the substantially flat portion. First end cap 420 also has an exterior surface 446 and an interior surface 448. First annular groove 492 is shaped to receive first lip portion 449 in a substantially air-tight configuration. First end 412 of outer sidewall 410 is flush with first end 426 of hollow fiber assembly 402 creating a first endwall 450. Thus, interior surface 448 of first end cap 420 and first endwall 450 bound a first gas chamber 458. First gas chamber 458 is in communication with first end 426 of hollow fiber assembly 402 and also in communication with a gas inlet 462.

Similarly, second end cap 422 is a substantially cup-shaped structure having a substantially second flat portion 453 and a second lip portion 455 formed integrally from the substantially flat portion. Second end cap 422 also has an exterior surface 452 and an interior surface 454. Second annular groove 494 is shaped to receive second lip portion 449 in an air-tight configuration. Second end 414 of outer sidewall 410 is flush with second end 428 of hollow fiber assembly 402 creating a second endwall 456. Thus, interior surface 454 of second end cap 422 and second endwall 456 define a second gas chamber 460. Second gas chamber 460 is in communication with second end 428 of hollow fiber assembly 402 and also in communication with a gas outlet 464. Gas inlet 462 and gas outlet 464 are showing having a fitting 466 and a fitting 468 disposed therein. Mounting collars 430, 432 are in airtight connection with gas chambers 458, 460, respectively. Thus, a gas flow circuit is created by gas inlet 462, gas outlet 464, and hollow fibers 12.

Disposed through outer sidewall 410 is a blood inlet 471. Intermediate sidewall 434 has a blood inlet 472. A blood inlet conduit 470 is in communication with blood inlet 471 and blood inlet 472, and consequently, in communication with second chamber 444. In order to reinforce blood inlet conduit 470 in housing 404, a reinforcing collar 474 is provided around blood inlet 472 at intermediate sidewall 434. A fitting 478 is disposed in blood inlet 471.

Disposed through second end cap 422 is a blood outlet 476. Mounting collar 432 has a blood outlet 482. A blood outlet conduit 480 is in communication with blood outlet 476 and 482 and, consequently, in communication with second chamber 444. A fitting 484 is disposed in blood outlet conduit 480. Thus, a blood flow circuit is formed by blood inlet conduit 470, second chamber 444, and blood outlet conduit 480. The blood flow circuit is kept completely separated from the gas flow circuit by the mounting collars 430, 432 and intermediate sidewall 434 except for the surface of the hollow fibers. In addition, the blood flow circuit is separated from the first chamber by intermediate sidewall 434.

In one embodiment, hollow fibers 12 are woven into a pattern similar to that described in U.S. Pat. No. 5,230,862, incorporated herein by specific reference. The woven pattern of hollow fibers 12 create a matrix 496. As shown in FIG. 9, matrix 496 has a substantially cylindrical configuration having a boundary 498. Hollow fibers 12 are woven such that matrix 496 surrounds a channel 486 centrally disposed within the matrix. Channel 486 is in communication with blood outlet 482. First mounting 430 has a solid portion 488 which prevents blood from escaping into first gas chamber 458.

As can be appreciated from the foregoing description, heart/lung blood gas exchanger 400 has a dual-chamber configuration such that first chamber 424 is adjacent to second chamber 444. In the embodiment shown in FIGS. 8 and 9, first chamber 424 surrounds second chamber 444. FIG. 9 is also useful in showing that hollow fibers 12 substantially surround channel 486. While FIG. 9 shows housing 404 and matrix 496 of hollow fibers 12 having a substantially circular cross section, other configurations may be equally suitable.

The various parts of housing 404 can be secured together by mechanical means such as, but not limited to, welding, injection molding, adhesive, heat sealing, and the like. Outer sidewall 410 is in secure engagement with end caps 420, 422. First end and second ends 412, 414 of outer sidewall 410 are also securely connected to first and second ends 426, 428 of hollow fiber assembly 402. First end 436 of intermediate sidewall 434 is securely connected between first end 412 of outer sidewall 410 and first end 426 of hollow fiber assembly 402. Similarly, second end 438 of intermediate sidewall 434 is securely connected between second end 414 of outer sidewall 410 and second end 428 of hollow fiber assembly 402. In any embodiment, it is important that the seal around second chamber 444 be blood-tight. Similarly, it is essential that the communication between gas chambers 458, 460, mounting collars 430, 432, and the hollow fibers 12 be air-tight such that no gas bubbles are formed in second chamber 444. It will be appreciated that seals, such as an O-ring, may be provided to reinforce the seals around the housing parts.

Outer sidewall 410 and end caps 420, 422 may be constructed of a rigid material such as plastic, polyvinylchloride, and the like. Housing 402 should be constructed of a transparent material such that the inner workings of the device may be easily viewed. Housing 402 should also be constructed of a biocompatible material. In one embodiment, intermediate sidewall 434 is constructed of an elastomeric material such as polyurethane. However, any suitable elastomeric material may be profitably employed within the scope of the invention. The elastomeric material may be transparent. Preferably, housing 402 is small in size. For example, a suitable size could be less than about 30 cm in height, 30 cm in width, and 30 cm length. Even more preferred, housing 402 is less than about 20 cm in height, 20 cm in width, and 20 cm in length.

Because intermediate sidewall 434 may be constructed of an elastomeric material, the combination of the intermediate sidewall 434 and hollow fiber assembly 402 operates substantially similar to the compliant blood gas exchanger 200 described in previous embodiments. Because of the elastomeric nature of intermediate sidewall 434, second chamber 444 may expand or contract depending on internal or external pressures as shown by the phantom lines in FIGS. 8 and 9.

The woven pattern of hollow fibers 12 and the elastomeric qualities of intermediate sidewall 434 advantageously assist in an optimal blood flow pattern throughout matrix 496. During operation, blood infuses into second chamber 444 through blood inlet 472. Intermediate sidewall 434 distends as the pressure is received by second chamber 444. When intermediate sidewall 434 distends, a reserve 499 is created to hold the excess amount of blood. The elasticity of intermediate sidewall 434 causes it to bias back into its original position. Such action forces the blood in reserve 499 to flow substantially perpendicularly through matrix 496 and to be collected centrally through channel 486. This particular blood flow pattern is desirable because it allows the blood to contact the hollow fibers 12 at a substantially transverse angle.

In operation, gas enters first gas chamber 458 and flows through the lumen of hollow fibers 12. Venous blood is introduced through blood inlet conduit 470 and into second chamber 444. Because blood inlet conduit 470 is substantially transverse to the hollow fibers 12, blood is constantly mixing and crosses the surfaces of many hollow fibers before it reaches channel 486. Oxygen is exchanged into the blood stream while carbon dioxide is exchanged into the lumen of the hollow fibers 12. Blood is directed out of second chamber 444 through channel 486 and out through blood outlet conduit 480. Carbon dioxide is removed from the device through hollow fibers 12 through second gas chamber 460 and out gas outlet 468.

In one embodiment, heart/lung blood gas exchanger 400 operates with a continuous pressurized blood flow. There exist many alternative ways to create a continuous pressurized flow. In one embodiment, first chamber 424 is completely enclosed by interior surface 418 of outer sidewall 410 and exterior surface 440 of intermediate sidewall 434. A pump or vacuum can be connected to blood inlet 472 or blood outlet 482 to create a continuous blood flow. Thus, second chamber 444 can be manipulated to expand or contract depending on the pressure of the pump or vacuum.

In another embodiment, heart/lung blood gas exchanger 400 operates with a pulsatile blood flow. In this embodiment, an inlet 490 is disposed in outer sidewall 410 to be in communication with first chamber 424. Accordingly, first chamber 424 may be filled with a fluid. The term fluid as herein defined refers to any suitable gas or liquid or combination thereof. For example, a suitable fluid may be saline. A pump or a vacuum can be connected to inlet 490. First chamber 424 can thus be manipulated to cause second chamber 444 to expand or contract depending on the fluid pressure of first chamber 424. For example, by applying a variable venous vacuum to first chamber 424, intermediate sidewall 434 is caused to distend toward outer sidewall 410. This increases the volume of second chamber 444 and causes blood inflow from blood inlet conduit 470. Alternatively, pressure can be increased in first chamber 424 such that intermediate sidewall 434 is caused to distend away from outer sidewall 410. This causes blood from second chamber 444 to exit through channel 486 and out blood outlet conduit 480.

A number of mechanisms may be profitably employed to cause pressure increase or decrease in either first chamber 424 or second chamber 444. In one embodiment, a continuous flow may be created by placing a high-speed axial flow pump or a roller pump in communication with blood inlet conduit 470 or blood outlet conduit 480. Alternatively, vacuum pump may be attached to inlet 490, blood inlet conduit 470 or blood outlet conduit 480. In another embodiment, a pulsatile pump may be formed using a pusher plate mechanism, activated by an electromagnetic solenoid system. Other mechanisms that may serve equally well to create a pulsatile pump are an electrically powered eccentric cam, or high-speed reversing electric impeller pump. Alternatively, a vacuum pump may be used to provide a pulsatile flow.

Figure 10:
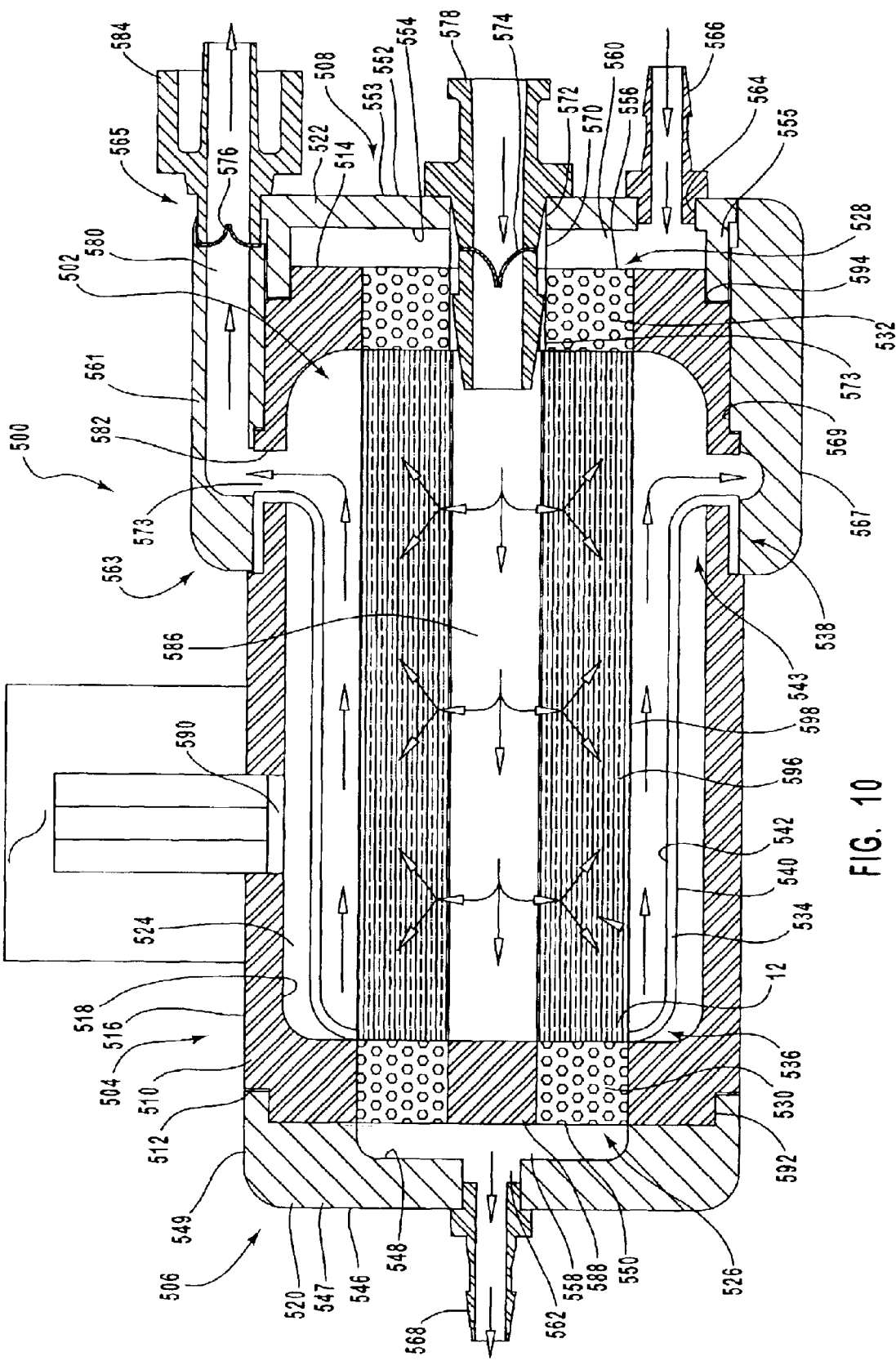
FIG. 10 is a cross sectional view of a heart/lung blood gas exchanger in accordance with another embodiment of the present invention.

An alternative embodiment of a heart/lung blood gas exchanger 500 is depicted in FIG. 10. As shown in FIG. 10, heart/lung blood gas exchanger 500 comprises a hollow fiber assembly 502 disposed in a housing 504. Housing 504 has a first end 506, a second end 508 with an outer sidewall 510 extending there between. Housing 504 terminates at first end 506 in a first end cap 520. Similarly, housing 504 terminates at second end 508 in a second end cap 522. Outer sidewall 510 has a first end 512, a second end 514, an exterior surface 516 and an interior surface 518. Interior surface 518 bounds a first chamber 524 that will be described hereinafter in more detail. Exterior surface 516 of first end 512 of outer sidewall 510 has a first annular groove 592. Similarly, exterior surface 516 of second end 514 of outer sidewall 510 has disposed thereat a second annular groove 594.

Housing 504 has hollow fiber assembly 502 disposed therein. Hollow fiber assembly 502 has first end 526 and second end 528. Hollow fiber assembly 502 comprises a mounting collar 530 at first end 526, a mounting collar 532 at second end 528, and a plurality of hollow fibers 12 disposed there between. Mounting collars 530, 532 surround the ends of hollow fibers 12.

First end cap 520 is a substantially cup-shaped structure having a substantially first flat portion 547 and a first lip portion 549 formed integrally with each other. First end cap 520 also has an exterior surface 546 and an interior surface 548. First annular groove 592 is shaped to receive first lip portion 549 in a substantially air-tight configuration. First end 512 of outer sidewall 510 is flush with first end 526 of hollow fiber assembly 502 creating a first endwall 550. Thus, interior surface 548 of first cap 520 and first endwall 550 bound a first gas chamber 558. First gas chamber 558 is in communication with first end 526 of hollow fiber assembly 502 and also in communication with a gas outlet 562.

Similarly, second end cap 522 is a substantially cup-shaped structure having a substantially flat portion 553 and a second lip portion 555 formed integrally from the substantially flat portion. Second end cap 522 also has an exterior surface 552 and an interior surface 554. Second annular groove 594 is shaped to receive second lip portion 555 in a substantially air-tight configuration. Second end 514 of outer sidewall 510 is flush with second end 528 of hollow fiber assembly 502 creating a second endwall 556. Thus, interior surface 554 of second end cap 522 and second endwall 556 define a second gas chamber 560. Second gas chamber 560 is in communication with second end 528 of hollow fiber assembly 502 and also in communication with a gas inlet 564. Gas inlet 564 and gas outlet 562 are shown having a fitting 566 and a fitting 568 disposed therein.

A blood inlet 572 is disposed through second end cap 522. A blood inlet 573 is disposed through second mounting collar 532. A blood inlet conduit 570 is in communication with blood inlet 572 and blood inlet 573, and, consequently, in communication with second chamber 544. A fitting 578 is disposed in blood inlet conduit 570. Fitting 578 comprises a one-way valve 574 to assist in directing blood into second chamber 544.

Disposed through outer sidewall 510 is a blood outlet 582. A collar 561 is disposed at second end 508 of housing 504. Collar 561 encircles second end 514 of sidewall 510 and end cap 522. Collar 561 has a first end 563, a second end 565, an exterior surface 567 and an interior surface 569. Disposed along one side of collar 561 is a blood outlet conduit 580 having a first end 573 disposed through interior surface 569 of collar 561 and a second end 575 disposed through second end 565 of collar 561. First end 573 of conduit 570 is in communication with blood outlet 582. Second end 575 of blood outlet conduit 580 is shown having a fitting 584 disposed therein. Fitting 584 comprises a one-way valve 576 to assist in directing blood out of second chamber 544.

Between outer sidewall 510 and hollow fiber assembly 502 is an intermediate sidewall 534. Intermediate sidewall 534 has a first end 536, a second end 538, exterior surface 540, and interior surface 542. First end 536 of intermediate sidewall 534 is securely fastened to first end 512 of outer sidewall 510. Second end 538 of intermediate sidewall 534 has a U-shaped portion 543. U-shaped portion 543 is shown securely fastened between first end 563 of collar 561 and exterior surface 516 of sidewall 510 to create an air-tight/blood-tight seal.

Hollow fibers 12 are woven into a pattern similar to that described for heart/lung blood gas exchanger 400. That is, a matrix 596 is formed having a substantially cylindrical configuration. Matrix 596 has an outer boundary 598. Hollow fibers 12 are woven such that matrix 596 surrounds a channel 586 centrally disposed within the matrix. Channel 586 is in communication with blood inlet conduit 570. First mounting 530 has a solid portion 588 which prevents blood from escaping into first gas chamber 558.

It will be appreciated from the foregoing description that a dual chamber configuration is created by outer sidewall 510 and intermediate sidewall 534. A first chamber 524 is established on the first end 506 of housing 504 between outer sidewall 510 and intermediate sidewall 534. Intermediate sidewall 534 bounds a second chamber 544 which extends from first end 506 to second end 508 of sidewall 510. Second chamber 544 houses hollow fibers 12. Thus, first chamber 524 is adjacent to second chamber 544. Disposed through sidewall 544 and in communication with first chamber 524 may a fluid inlet 590 useful for forming a pulsatile flow.

First chamber 524 and second chamber 544 operate substantially similar to heart/lung blood gas exchanger 400 described above. As described above, fluid inlet 590 may be in communication with a fluid which, in turn, is connected to a pump or vacuum. In this manner, the volume of first chamber 524 may be increased or decreased which affects the volume of second chamber 544 adjacent to the first chamber. As discussed above, there are a variety of mechanisms which may be suitable to create a pulsatile flow within first chamber 524. Alternatively, a pump or vacuum may be connected to blood inlet 572 or blood outlet 582 to create a pulsatile or continuous flow within second chamber 544. This may occur with or without fluid inlet 590.

The various parts of housing 504 can be secured together by mechanical means such as, but not limited to, welding, injection molding, adhesive, heat sealing, and the like. Outer sidewall 510 is in secure engagement with end caps 520, 522. First end and second end 512, 514 of outer sidewall 510 are also securely connected to mounting collars 530, 532. First end 536 of intermediate sidewall 534 is securely connected between first end 512 of outer sidewall 510 and first mounting collar 530. Similarly, second end 538 of intermediate sidewall 534 is securely connected first end 563 of collar 561 and exterior surface 516 of outer sidewall 510. In any embodiment, it is important that the seal around second chamber 544 be blood-tight. Similarly, it is essential that the communication between gas chambers 538, 560, mounting collars 530, 532, and the hollow fibers 12 be air-tight such that no bubbles are formed in second chamber 544.

Outer sidewall 510 is constructed of a rigid material such as polyvinylchloride. Intermediate sidewall 534 is constructed of an elastomeric, transparent material such as polyurethane. The elastomeric nature of intermediate sidewall 534 allows second chamber 544 to expand or contract in response to pulsatile forces. Outer chamber 524 may be filled with a fluid. The term fluid as herein defined refers to any suitable gas or liquid or combination thereof. For example, a suitable fluid may be saline. Because intermediate sidewall 534 is constructed of an elastomeric material, the combination of the intermediate sidewall 534 and hollow fiber assembly 502 operates substantially similar to the compliant blood gas exchanger 100 or 200 described in previous embodiments.

While FIGS. 9 and 10 show a first chamber disposed within a second chamber, the present invention is not limited to that particular embodiment. Rather, the present invention contemplates any structure in which the first chamber is adjacent to the second chamber and influencing pressures within one influences the other. For example, included within the scope of this invention is an embodiment where the first chamber is adjacent to the second chamber, but neither one surrounds the other. The first chamber could be in communication with a pumping mechanism in order to create a pulsatile flow in the second chamber, or vice versa.

It will be appreciated that the dimensions of the hollow fibers, surface area of the hollow fibers exposed to blood, packing density of the hollow fiber bundles, and the size and configuration for the blood and gas conduits may be modified in order to achieve optimum performance depending on the size of the patient and the location if the device in relation to the patient's body. The specifications for various examples of heart/lung blood gas exchanger 400 and 500 are reproduced below. Table A contains hollow fiber assembly specifications for three sizes of heart/lung blood gas exchanger 400 or 500. Table B and C contain performance specifications for three sizes of heart/lung blood gas exchangers. Finally, Table D compares the performance specifications for two sizes of heart/lung blood gas exchangers compared to a conventional cardiopulmonary bypass (CPB) system.

TABLE A

Heart/lung Blood Gas Exchanger Hollow Fiber Assembly Specifications

|  | Neonatal | Mid-Size | Adult |
|---|---|---|---|
| Surface Area, $m^2$ | 0.1 | 1.7 | 3.4 |
| # fibers with 190 mm inner diameter | 1435 | 26,600 | 26,600 |
| # fibers with 250 mm inner diameters | 410 | 7,600 | 7,600 |
| Total # fibers | 1845 | 34,200 | 34,200 |
| Bundle length, cm | 5 | 5 | 10 |
| Potting length × 2, cm | 3 | 3 | 3 |
| Fiber length, cm | 16 | 20 | 28 |

TABLE B

Performance Specifications for Three Sizes of Heart/lung Blood Gas Exchangers

| Performance Parameter | Small Neonatal | Intermediate Pediatric | Large Adult |
|---|---|---|---|
| Blood Flow Rate | 30–300 ml/min | 0.3–3.0 L/min | 3.0–10.0 L/min |
| Blood Inlet outlet pressure gradient | <100 mmHg | <140 mmHg | <165 mmHg |
| Gas Flow Rate | 0.1–0.5 L/min | 0.5–5.0 L/min | 3.0–10.0 L/min |

TABLE B-continued

Performance Specifications for Three Sizes of Heart/lung Blood Gas Exchangers

| Performance Parameter | Small Neonatal | Intermediate Pediatric | Large Adult |
|---|---|---|---|
| Gas Inlet-Outlet Pressure Gradient | <10 mmHg | <10 mmHg | <10 mmHg |
| $O_2$ Exchange Rate | 3.0 to 15.0 ml/min | 100 to 250 ml/min | >300 ml/min |
| $CO_2$ Exchange Rate | 2.8 to 12.0 ml/min | 100 to 230 ml/min | >280 ml/min |
| Rated Blood Flow (blood gas exchange capacity) | 20 to 60 ml/min | 1.0 to 3.0 L/min | 5.0 to 8.0 L/min |

TABLE C

Performance Specifications for Three Sizes of Heart/lung Blood Gas Exchangers

| | Neonatal | Pediatric | Adult |
|---|---|---|---|
| Overall Dimensions | 5 × 9 cm | 8 × 10 cm | 10 × 15 cm |
| Gas Exchange Surface Area | 0.5 m$^2$ | 1.7 m$^2$ | 2.5 m$^2$ |
| Blood Flow Rate | 60 ml/min to 1.5 L/min | 1.6–2.8 L/min | 3.9–6.1 L/min |
| Gas Flow Rate (Sweep) | 100–300 ml/min | 0.5–1.5 L/min | 2.2–6.6 L/min |
| Priming Volume | 8 ml | 40 ml | 120 ml |
| Gas ($O_2$ & $CO_2$) Exchange Rate | 6–15 cc/min. | 84–178 ml/min | 181–346 ml/min |
| Rated Flow | 1.4 L/min | 3.1 L/min | 5.0 L/min |
| Hollow Fiber Pressure Drop | 20–100 torr vacuum | 30–150 torr vacuum | 40–200 torr vacuum |
| Blood Pressure Drop Across Exchanger | 8–64 torr | 45–72 torr | 18–80 torr |

TABLE D

Performance Specifications of Two Sizes of Heart/lung blood gas exchanger Compared to Conventional CPB Systems

| Performance Parameter | Adult Size | Pediatric Size | Conventional CPB Machine |
|---|---|---|---|
| A. General Specifications | | | |
| Over-all Dimensions | 12 × 15 × 20 cm | 3 × 5 × 8 cm | 2 × 3 × 4 ft |
| Weight of Device | 500 grams | 200 grams | 200 kilograms |
| Priming Volume | 150 cc | 15 cc | 100 cc to 1,500 cc |
| Composition of Gas Exchange Membrane | Siloxane membrane 1 micron thick supported by microporous polypropylene hollow fibers | | Microporous polypropylene hollow fibers or thick sheets of siloxane |
| Thrombogenicity | Nil | Nil | moderate |
| | All Blood Contacting Surfaces Coated with CardioPulmonics' Thromboresistant Coating (TRC) | | |

TABLE D-continued

Performance Specifications of Two Sizes of Heart/lung blood gas exchanger Compared to Conventional CPB Systems

| Performance Parameter | Adult Size | Pediatric Size | Conventional CPB Machine |
|---|---|---|---|
| B. Exchanger Specifications | | | |
| Gas Flow through the device (range) | 3 to 10 L min | 0.1 to 3.0 L/min | 0.4 to 8.0 L/min |
| Gas Pressure Gradient (inlet-outlet) | 10 torr | 8 torr | 10 to 30 torr |
| Volume, Gas Compartment | 40 cc | 4 cc | 10 to 200 cc |
| Surface Area of Gas Exchange Membrane | 1 m$^2$ | 2,500 cm$^2$ (0.25 m$^2$) | 0.5 to 5.0 m$^2$ |
| Number of Hollow Fibers | 30,000 | 10,000 | 4,000 to 80,000 |
| I.D. of Hollow Fibers | 120 Microns 190 Microns 400 Microns | 120 Microns 290 Microns 400 Microns | 190 to 300 Microns |
| Rate of $O_2$ Exchange (into blood) | 200 to 450 cc/min | 20 to 200 cc/min | 30 to 400 cc/min |
| Rate of $CO_2$ Exchange (out of blood) | 190 to 400 cc/min | 18 to 190 cc/min | 20 to 400 cc/min |
| C. Blood Pump Specification | | | |
| Stroke Volume | 20 to 66 cc | 2 to 10 cc | N/A |
| Pulse Rate (blood) | 50 to 150 beats/min | 50 to 150 beats/min | N/A |
| Blood Flow Through the Device (range) | 1.0 to 10.0 L/min | 0.1 to 1.5 L/min | 0.2 to 8.0 L/min |
| Blood Pressure Gradient (inlet-outlet) | 10 to 30 torr | 5 to 20 torr | 100 to 500 torr |
| Type of Pump | Pulsatile, bladder type with pusher plate | Pulsatile, bladder type with pusher plate | Continuous flow (roller pump or centrifugal pump) |

The optimized fiber winding pattern, the biocompatible nature of the system, and the compliant nature of the system all contribute to a more effective, less labor intensive, less costly blood gas exchanger. In addition, the present invention provides blood gas exchange with less blood damage, higher flow rates, pulsatile flow, and less bleeding or thromboembolic complications.

The above-described embodiments for a heart/lung blood gas exchanger 400 or 500 may also be useful as an extracorporeal portable cardiopulmonary bypass (CPB) system. The heart/lung blood gas exchanger can be utilized as a portable, fully integrated, automated mechanical heart-lung system which performs all the hemodynamic and blood gas exchange function of the current conventional large, complex extracorporeal CPB systems. The heart/lung blood gas exchanger has the essential functional components (i.e., oxgyenator and blood pump) included in the conventional CPB machine. However, the heart/lung blood gas exchanger 400 or 500 is portable, safe, and easy to operate. Furthermore, the heart/lung blood gas exchanger is operable at variable speeds controlled automatically by the patient's blood pressure.

Emergency application of heart/lung blood gas exchanger 400 or 500 would be extremely useful when transporting cardio-respiratory failure patients by helicopter, airplane, or ambulance. Traditional CPB systems are too large and cumbersome for this application. In addition, the present invention would be extremely useful for use with de jur dead organ donors to maintain perfusions of donor organs to prolong the time of viability.

Furthermore, when used as a CPB system, connecting the blood inlet and blood outlet to the blood system to the patient merely requires a simple percutaneous cannulation which is less invasive than surgery. Thus, the present invention is simple enough for a well-trained medical technician to operate. This allows a quicker, more effective, and easier operation of a CPB system to support emergency cardiorespiratory failure patients in the ICU, emergency situations outside the operating room, in cardiac catheterization/angioplasty, invasive cardiology laboratories, emergency rooms, in the field outside a hospital, and at accident sites.

In addition, the present invention allows extracorporeal CPB perfusions in situations where they have not previously been possible using conventional CPB systems. For example, the present invention may be used in acute respiratory failure in very small neonates or premature infants, patients with sudden serious arrhythmias, and/or myocardial inadequacies in the ICU, cardiac catheterization/angioplasty laboratory; bridge to heart, lung, or heart-lung transplant.

It will be appreciated that a compact, portable, and efficient blood gas exchanger system that is appropriate in such a wide variety of applications would have a significant and widespread impact on the clinical medical practice. Specifically, the present invention increases safety and efficacy of CPB procedures while significantly reducing the cost, risks and hazards associated with such procedures. Further, the present invention provides an important procedure that would not otherwise be available with conventional CPB systems.

Figure 11:
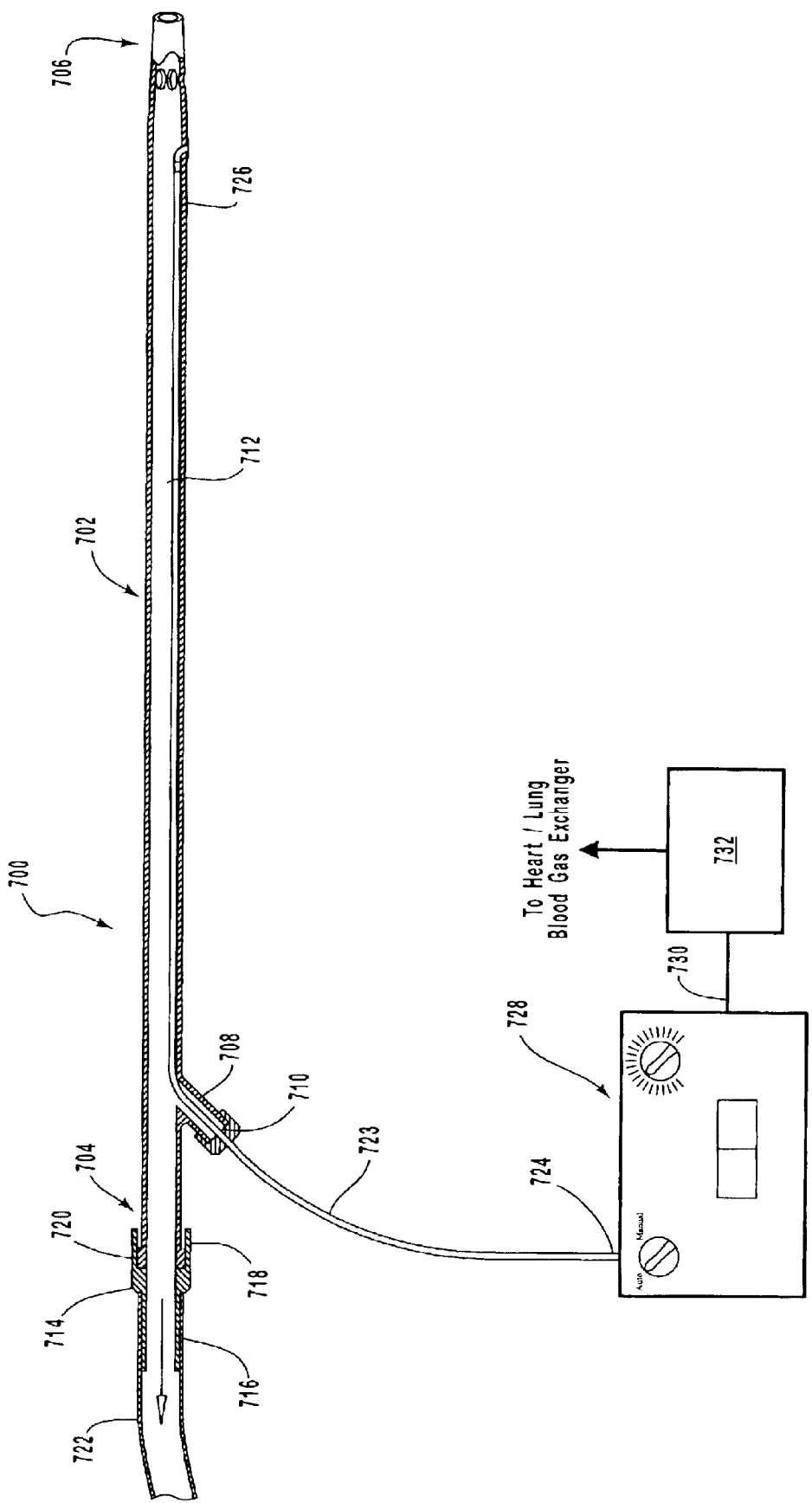
FIG. 11 is a view of a right atrial pressure-sensing cannulation system in accordance with yet another aspect of the present invention.

In one embodiment, the pulsatile flow is synchronized with the blood pressure of the patient. An example of this embodiment is depicted in FIG. 11 in which a pressure sensing cannula system 700 is shown. Cannula system 700 has a blood uptake cannula 702 which is substantially tubular and forms a conduit 712. Blood uptake cannula 702 has a first end 704 and a second end 706. Disposed between first end 704 and second end 706 along blood uptake cannula 702 is a sidearm 708 having an inlet 710. Inlet 710 is in communication with conduit 712. First end 704 of blood uptake cannula 702 has formed thereat an annular ridge 720.

Securely connected to first end 704 of blood uptake cannula 702 is a fastening collar 714. Fastening collar 714 has a male connector portion 716 and a female connector portion 718. First end 704 of blood uptake cannula 702 is received within female connector portion 718. Annular ridge 720 is slightly larger than female connector portion 718 so that a secure connection is formed there between. Male connector portion 716 is disposed within blood inlet conduit 722. Blood inlet conduit 722 is a tubular structure. Further, fastening collar 714 is hollow such that blood communication is established between blood uptake cannula 702 and blood inlet conduit 722. It will be appreciated that blood inlet conduit 722 may be the same as or connected to blood inlet conduits 470 and 570 of heart/lung blood gas exchangers 400 and 500 described above. Thus, the operation of heart/lung blood gas exchangers 400 and 500 is substantially similar when blood uptake cannula 702 is employed.

Disposed within the length of blood uptake cannula 702 and emerging from sidearm 708 is a pressure sensor 723. Pressure sensor 723 has a first end 724 connected to a control box 728 and a second end 726 attached to second end 706 of blood uptake cannula 702. Pressure sensor 723 comprises a small lead wire or tubing which is embedded into the wall. Alternatively, pressure sensor 723 extends slightly beyond second end 706 of blood uptake cannula 702 and attaches to the outer surface of the blood uptake cannula 702.

A control box 728 provides controls for automatic or manual regulation of the rate of a pump mechanism 732 which is connected to a heart/lung blood gas exchanger 400 or 500. The control box 728 has a display which shows the RPM of the pump mechanism 732. The control box 728 also should have a display to show the central venous/right atrial pressure. The control box 728 has a line 730 which leads to the pump mechanism 732. The pressure sensor 723 recognizes pressure changes in the blood vessel and delivers a pressure sensing signal to control box 728. The pressure sensing signal is translated to a pump speed control signal which is delivered through line 730 to the pump mechanism 732. The pump speed control signal increases or decreases the pulse rate of the pump mechanism 732 in response to the pump speed control signal.

In one embodiment, blood uptake cannula 702 is inserted percutaneously into the right atrium. In one embodiment, pressure sensor 723 reads a range of pressure from about −3 to +20 torr. Pressure sensor 723 may be self-zeroing regardless of the position of the patient. In addition, the pressure sensor should be sensitive to small pressure changes (e.g., 1 to 2 torr). The pressure sensor should have minimal drift and long-term stability. Further, the pressure sensor should be protected from atrial wall pressure and/or collapse and from blood flow currents. The blood uptake cannula 702 should have a thromboresistant coating. In one embodiment, blood uptake cannula 702 has an outer diameter from about 4.0 mm to about 12.5 mm depending on the size of the patient. Blood uptake cannula 702 generally has a length of about 10 cm to about 30 cm depending on the size of the patient.

It will be appreciated that cannula system 700 is but one embodiment for synchronizing the pulsatile flow of the heart/lung blood gas exchanger with the pulse of the patient.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A compliant blood gas exchanger for enabling oxygen and carbon dioxide exchange in circulating venous blood, the compliant blood gas exchanger comprising:

a housing having a first end, a second end, and an elastomeric sidewall extending there between, the elastomeric sidewall bounding a chamber, the chamber being in communication with a blood inlet and a blood outlet;

a first mounting collar disposed at least partially within the housing at the first end of the housing, the first mounting collar being in communication with a gas inlet;

a second mounting collar disposed at least partially within the housing at the second end of the housing, the second mounting collar being in communication with a gas outlet; and a plurality of hollow fibers, each of the plurality of fibers having a first end secured by the first mounting collar and a second end secured by the second mounting collar, the plurality of hollow fibers comprising two sizes of fibers interwoven together, each of the plurality of fibers having a porous surface through which the plurality of hollow fibers is capable of gaseous exchange but not liquid exchange.

2. The compliant blood gas exchanger as recited in claim 1, further comprising the plurality of hollow fibers being constructed from a biocompatible material.

3. The compliant blood gas exchanger as recited in claim 2, wherein the plurality of hollow fibers are coated with an effective, non-leachable thromboresistant coating.

4. The compliant blood gas exchanger as recited in claim 3, wherein the plurality of hollow fibers are coated with heparin.

5. The compliant blood gas exchanger as recited in claim 1, further comprising:
   a first end cap disposed at the first end of the housing, the first end cap being disposed between the first mounting collar and the gas inlet; and
   a second end cap disposed at the second end of the housing, the second end cap being disposed between the second mounting collar and the gas outlet.

6. The compliant blood gas exchanger as recited in claim 1, further comprising each of the plurality of hollow fibers being crimped.

7. The compliant blood gas exchanger as recited in claim 1, further comprising the plurality of hollow fibers being configured into segments comprised of expanded portions and narrow portions.

8. The compliant blood gas exchanger as recited in claim 1, further comprising the plurality of hollow fibers comprising two sizes of hollow fibers woven together.

9. The compliant blood gas exchanger as recited in claim 1, further comprising the matrix comprising a channel extending through the matrix, the channel being in communication with the blood inlet or blood outlet.

10. The compliant blood gas exchanger as recited in claim 1, wherein the elastomeric sidewall is spaced apart from the matrix such that a reserve is formed in the chamber between the elastomeric sidewall and the matrix.

11. The compliant blood gas exchanger as recited in claim 1, further comprising the gas inlet being connected to a gas source, the gas outlet being connected to an exhaust source, the blood inlet being connected to an arterial blood source, and the blood outlet being connected to a venous blood source.

12. The compliant blood gas exchanger as recited in claim 1, further comprising the blood inlet being connected to a pump mechanism.

13. The compliant blood gas exchanger as recited in claim 1 wherein the chamber has length and one of the blood inlet and the blood outlet is positioned at a midpoint along the length of the chamber.

* * * * *